(12) United States Patent
Li et al.

(10) Patent No.: US 11,426,488 B2
(45) Date of Patent: Aug. 30, 2022

(54) BIOACTIVE MICRO-NANO PORE GRADIENT OXIDE CERAMIC FILM

(71) Applicant: Hangzhou Erran Technology Co., Ltd., Hangzhou (CN)

(72) Inventors: Tingkai Li, Hangzhou (CN); Zhijian Shen, Hangzhou (CN); Jie Zhang, Hangzhou (CN); Wuyuan Zhao, Hangzhou (CN); Li Tao, Hangzhou (CN)

(73) Assignee: Hangzhou Erran Technologies Co., Ltd., Hangzhou (CN)

( * ) Notice: Subject to any disclaimer, the term of this patent is extended or adjusted under 35 U.S.C. 154(b) by 0 days.

(21) Appl. No.: 16/615,436

(22) PCT Filed: May 18, 2018

(86) PCT No.: PCT/CN2018/087401
§ 371 (c)(1),
(2) Date: Nov. 21, 2019

(87) PCT Pub. No.: WO2018/214808
PCT Pub. Date: Nov. 29, 2018

(65) Prior Publication Data
US 2020/0179564 A1 Jun. 11, 2020

(30) Foreign Application Priority Data

May 22, 2017 (CN) .......................... 201710362313.5
May 22, 2017 (CN) .......................... 201710362316.9

(51) Int. Cl.
*C01F 7/34* (2006.01)
*A61L 27/30* (2006.01)
(Continued)

(52) U.S. Cl.
CPC ............. *A61L 27/306* (2013.01); *A61L 27/56* (2013.01); *B08B 3/12* (2013.01); *C01F 7/34* (2013.01);
(Continued)

(58) Field of Classification Search
CPC ........ A61L 27/306; A61L 27/56; A61L 27/32; C01G 23/02; C01G 23/047; C01G 23/04;
(Continued)

(56) References Cited

U.S. PATENT DOCUMENTS

| 2002/0031675 A1* | 3/2002 | Cales | ........................ A61F 2/32 |
| | | | 428/472 |
| 2003/0151155 A1* | 8/2003 | Muroi | ................... C04B 35/632 |
| | | | 264/44 |

(Continued)

FOREIGN PATENT DOCUMENTS

| CN | 107056258 | 8/2017 |
| CN | 107141024 | 9/2017 |
| CN | 107374763 | * 11/2017 ............... B22F 9/00 |

OTHER PUBLICATIONS

Thakare et al., Progress in Synthesis and Applications of Zirconia, 2012, International Journal of Engineering Research and Development, vol. 5 Issue 1, pp. 25-28 (Year: 2012).*

(Continued)

*Primary Examiner* — Dah-Wei D. Yuan
*Assistant Examiner* — Andrew J Bowman
(74) *Attorney, Agent, or Firm* — Law Office of Gerald Maliszewski; Gerald Maliszewski

(57) ABSTRACT

The invention discloses micron-nano pore gradient oxide ceramic films with biological activity, which are prepared by the following methods: The surface structures are biomedical engineering materials; Inorganic precursor coating solutions or the organic precursor coating solutions are prepared (Continued)

with or without micron and nanopore additives; The surface structures of the substrate are treated in the following steps: (1) The surfaces of the substrate are coated by the inorganic precursor coating solutions or the organic precursor coating solutions with or without micron and nanopore additives; (2) The substrate with coatings are dried, sintered, naturally cooled, and cleaned. (3) The biomedical engineering materials with the micron-nanopore gradient oxide ceramic films, especially biomimetic micro-nanoporous gradient alumina film, yttrium partially stabilized zirconia film, and alumina doped yttrium partially stabilized zirconia films in this invention greatly improve biocompatibility and biological activity.

13 Claims, 2 Drawing Sheets

(51) Int. Cl.
    *A61L 27/56*     (2006.01)
    *B08B 3/12*     (2006.01)
    *C01G 25/00*     (2006.01)

(52) U.S. Cl.
    CPC ........ *C01G 25/006* (2013.01); *A61L 2420/02* (2013.01); *C01P 2002/52* (2013.01); *C01P 2004/64* (2013.01); *C01P 2004/84* (2013.01)

(58) Field of Classification Search
    CPC .......... B05D 3/00; B82Y 30/00; C04B 35/63; A61F 2/28; B22F 9/00
    See application file for complete search history.

(56) References Cited

U.S. PATENT DOCUMENTS

2006/0121080 A1*   6/2006   Lye ........................... A61F 2/07
                                                    623/1.39
2007/0151418 A1*   7/2007   Diaz .................... B01J 37/0221
                                                    75/370
2009/0177273 A1*   7/2009   Piveteau ................. A61L 27/56
                                                    623/1.46

OTHER PUBLICATIONS

Moorehead et al., Characterization of Novel Gel-Casting System to Make COmplex-Shaped ALuminum Oxide (Al2O3) Parts, 2016, US Army Research Laboratory, pp. 1-26 (Year: 2016).*

* cited by examiner

BIOACTIVE MICRO-NANO PORE GRADIENT OXIDE CERAMIC FILM

TECHNICAL FIELD

The invention relates to the field of biomedical engineering, in particular to a micro-nano pore gradient oxide ceramic film with biological activity.

BACKGROUND TECHNOLOGY

Bioengineering materials are kinds of materials, and material surface or structure which involves interaction with biological system. As a science, bioengineering materials have a history of about fifty years. The study of biomaterials is called biomaterial science or biomaterial engineering, and has been extensively and deeply studied. In its history, many governments, research institutes and companies have invested a lot of money in the research and development of new materials and products. Biomaterials science includes medicine, biology, chemistry, tissue engineering and materials science. Any material in contact with living tissue, organism or microorganism must consider its biocompatibility and biological activity.

There are two ways to improve the biocompatibility and bioactivity of bioengineering materials: one is to use the materials with similar chemical compositions and structures of organisms. For example, using the hydroxyapatite coating on a hip implant to improve the biocompatibility and bioactivity of the hip joint. However, these materials have low strength and fracture toughness, and poor bonding strength with matrix materials, which limits their applications. The other way is to use chemically inert materials with similar micro-structures of organisms to improve their biocompatibility and bioactivity. Biomaterials may be autologous, allogenic or xenograft materials for transplantation.

Self-assembly is one of the most commonly used terms in the modern science. Without any external force, the particles (atoms, molecules, colloids, micelles, etc.) can aggregate spontaneously and form thermodynamically stable structures. For example, the seven crystal systems in metallurgy and mineralogy (such as face-centered cube, body-centered cube, etc.) is an example of atomic self-assembly. Molecular self-assembly also exists widely in biological systems and forms many varieties of complex biological structures. We can find biological materials with the superior mechanical properties, which have special micro-structures. At the same time, the self-assembly has become a new strategy of the chemical synthesis and nanotechnology. The examples of these technologies include all the highly ordered structures of molecular crystals, liquid crystals, colloids, micelles, emulsions, phase separated polymers, thin films and self assembled monolayers. Almost all of the natural materials have a cross-scale hierarchical structure. In biomaterials, this cross-scale hierarchical structures are inherent. In the history of the biological structure researches. Astbury and Woods used X-ray scattering to determine the hierarchical structure of hair and wool. Protein is the basic unit of organism. The diameter of protein molecule is about 1-100 nanometers. Bone collagen is formed by organic molecules of 1.5 nanometers in diameter with triple helix structure. These bone collagen molecules are intermingled with mineral phases (such as hydroxyapatite and calcium phosphate) to form spiral fibrous structural units in alternating directions. These "units" are the basic building blocks of the skeleton, and the ratio of the organic and inorganic phases are about 60:40 in volume fractions. Further studies show that the hydroxyapatite crystal is a plate structure with a diameter of about 70-100 nanometers and a thickness of 1 nanometer. Almost all of the biomaterials have the similar nano-structure. The molecules of bone collagen can be adsorbed by these nanostructures and grow in the interstitial space of the molecules of hydroxyapatite crystals, which shows good biological activity. Therefore, the biomimetic nanostructured films can make chemical inert bioengineering materials have good biocompatibility and biological activity.

Biomaterials have been widely used recently, such as joint replacement, bone plate, bone cement, artificial ligaments and tendons, dental implants, vascular prosthesis, heart valves, skin repair devices (artificial tissue), cochlear replacement, contact lenses, breast implants, drug delivery mechanisms, vascular transplantation, stents, nerve conduits, surgical sutures, clips, and wound sutures, etc. Zirconia has been widely used in the field of bioengineering materials in recent years because of its high strength and fracture toughness. On the other hand, zirconia is chemically inert and biocompatible materials, but zirconia has no biological activity, which limits its applications.

SUMMARY OF THE INVENTION

The present invention is to provide a nano-oxide ceramic film with biological activity, which greatly improves the biocompatibility and biological activity of biomedical engineering materials, especially for zirconia.

The present invention provides the following processes:

The process using inorganic precursors:

The biologically active nano-oxide ceramic films are prepared by the following methods:

(1) The surface structures of biomedical engineering materials are formed by computer-aided design and computer-aided manufacturing. The surface structures can be macro-structure of rough surface, abnormal structure or smooth surface. The designs of surface structures are based on the needs of Biomedical Engineering materials.

(2) Inorganic precursor coating solutions with or without pore forming additives are prepared. The inorganic precursor coating solution is one of nanometer alumina suspension slurry, yttrium partially stabilized zirconia suspension slurry and alumina doped yttrium partially stabilized zirconia suspension slurry.

(3) The inorganic precursor coating solutions were used to coat the surface of the substrate after step (1) process. After drying, and high temperature sintering, natural cooling and cleaning, the single coating film with nano-pores or the double and more coating films with micro-pores in the inner layer and nano-pores in the outer layer was prepared.

As an embodiment, step (3) uses inorganic precursor coating solutions to coat the surface of the substrate after step (1) process. After drying, and sintering at high temperature, cooling naturally, and cleaning to obtain a single coating film with nano-grains and nano-pores, or a double coating films with micro-grains and micro-pores in the inner layer, and nano-grains and nano-pores in the outer layer was prepared.

As a preferred choice, the nano-sized alumina suspension slurry is prepared by liquid phase coprecipitation or hydrothermal-hydrolysis method.

The liquid phase co-precipitation method is as follows: The aluminum solutions are kinds of aluminum hydroxide suspension, aluminum chloride solution and aluminum nitrate solution, and the precipitate is ammonium hydroxide. In the first, the precipitate is slowly dropped into aluminum solution, stirred strongly to make it fully react, aged more than 8-12 hours after reaction, separated rapidly by centrifuging, filtering precipitation in vacuum, washed with distilled water and ethanol, and dried to obtain alumina precursor; and then the alumina precursor was made into slurry with 2-15 vol % of solid phase content by mixing 1-3 wt % of dispersant such as $CA(C_6H_8O_7.H_2O)$ and deionized water; after that adjusting PH of the slurry to 3-6, and put into ball milling such as in planetary mill for 10-30 h, finally adjusting PH of the slurry to 8-10 and adding and mixing 1-5 wt % of pore forming additives based on the weight of alumina to obtain nano-sized alumina suspension slurry.

The hydrothermal-hydrolysis method is as follows: In the first, the aluminum hydroxide suspension with concentration of 0.5-1 mol/L is put into the reactor, and heated the reactor to 40-60° C. for 2-3 hours, and then added 0.5-1 wt % of dispersant such as $CA(C_6H_8O_7.H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain alumina precursor; then the alumina precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized alumina suspension slurry is obtained.

As a preferred choice, the yttrium partially stabilized zirconia suspension slurry is prepared by liquid phase coprecipitation method or hydrothermal-hydrolysis method.

The liquid phase co-precipitation method is as follows: The zirconium solutions are kinds of zirconium hydroxide suspension, zirconium chloride solution and zirconium nitrate solution, and the yttrium solutions are kinds of yttrium hydroxide suspension, yttrium chloride solution and yttrium nitrate solution, and the precipitate is ammonium hydroxide. In the first, the precipitate is slowly dropped into mixed zirconium with 2-6 mol % of yttrium content solution, stirred strongly to make it fully react, aged more than 8-12 hours after reaction, separated rapidly by centrifuging, filtering precipitation in vacuum, washed with distilled water and ethanol, and dried to obtain yttrium partially stabilized zirconia precursor; and then the yttrium partially stabilized zirconia precursor was made into slurry with 2-15 vol % of solid phase content by mixing 1-3 wt % of dispersant such as $CA(C_6H_8O_7. H_2O)$ and deionized water; after adjusting PH of the slurry to 3-6, and put into ball milling such as in planetary mill for 10-30 h, finally adjusting PH of the slurry to 8-10 and adding and mixing 1-5 wt % of pore forming additives based on the weight of yttrium partially stabilized zirconia precursor to obtain nano-sized yttrium partially stabilized zirconia suspension slurry.

The hydrothermal-hydrolysis methods choose one from the following processes: The hydrothermal-hydrolysis methods 1: In the first, the Zirconium hydroxide suspension with concentration of 0.5-1 mol/L is put into the reactor, then yttrium oxide was added and mixed into the reactor 3-5 times respectively, and heated the reactor to 40-60° C. for 2-3 hours, and then added 0.5-1 wt % of dispersant such as $CA(C_6H_8O_7.H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain yttrium-stabilized zirconia precursor with yttrium content of 2-6 mol % was obtained; then the yttrium-stabilized zirconia precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized yttrium-stabilized zirconia precursor with yttrium content of 2-6 mol % suspension slurry is obtained.

The hydrothermal-hydrolysis methods 2: In the first, the 0.5-0.6 mol/L zirconium oxychloride solution and 1 mol/L carbonyl two amine with volume ratio of 1:1 were added to the reactor, and the reactor was heated into 150° C. for 2-4 hours, the zirconium hydroxide gel was generated. The gel was removed and mixed with the above original reaction liquid with the weight ratio of 1:1, and then was put into the flask equipped with a reflux condenser. Under stirring conditions, the hydrous zirconia sol was obtained by hydrolysis at boiling temperature of 100-150 C; After that 2-6 mol % yttrium nitrate solution was added into the hydrated zirconia sol. With stirring until yttrium nitrate was completely dissolved, the precipitation was gradually hydrolyzed and formed; Finally the precipitate can be separated quickly by centrifuging, filtering in vacuum, and washed with distilled water and ethanol, and dried to obtain yttrium-stabilized zirconia precursor with yttrium content of 2-6 mol % was obtained; then the yttrium-stabilized zirconia precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized yttrium-stabilized zirconia precursor with yttrium content of 2-6 mol % suspension slurry is obtained.

As a preferred choice, the alumina-doped yttrium partially stabilized zirconia suspension slurry is prepared by liquid phase coprecipitation or hydrothermal-hydrolysis method.

The liquid phase co-precipitation method is as follows: The zirconium solutions are kinds of zirconium hydroxide suspension, zirconium chloride solution and zirconium nitrate solution, and the yttrium solutions are kinds of yttrium hydroxide suspension, yttrium chloride solution and yttrium nitrate solution. The aluminum solutions are kinds of aluminum hydroxide suspension, aluminum chloride solution and aluminum nitrate solution, and the precipitate is ammonium hydroxide. In the first, the precipitate is slowly dropped into mixed 1-5 mol % aluminum and zirconium with 2-6 mol % of yttrium content solution, stirred strongly to make it fully react, aged more than 8-12 hours after reaction, separated rapidly by centrifuging, filtering precipitation in vacuum, washed with distilled water and ethanol, and dried to obtain alumina-doped yttrium partially stabilized zirconia precursor; and then the alumina-doped yttrium partially stabilized zirconia precursor was made into slurry with 2-15 vol % of solid phase content by mixing 1-3 wt % of dispersant such as $CA(C_6H_8O_7.H_2O)$ and deionized water; after adjusting PH of the slurry to 3-6, and put into ball milling such as in planetary mill for 10-30 h, finally adjusting PH of the slurry to 8-10 and adding and mixing 1-5 wt % of pore forming additives based on the weight of alumina-doped yttrium partially stabilized zirconia precursor to obtain nano-sized alumina-doped yttrium partially stabilized zirconia suspension slurry.

The hydrothermal-hydrolysis methods choose one from the following processes: The hydrothermal-hydrolysis methods 1: In the first, the 1-5 mol % aluminum mixed zirconium hydroxide suspension with concentration of 0.5-1 mol/L is put into the reactor, then yttrium oxide was added and mixed into the reactor 3-5 times respectively, and heated the reactor to 40-60° C. for 2-3 hours, and then added 0.5-1 wt % of dispersant such as $CA(C_6H_8O_7.H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain alumina-doped yttrium partially stabilized zirconia precursor with 1-5 mol % aluminum and yttrium content of 2-6 mol % was obtained; then the alumina-doped yttrium partially stabilized zirconia precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized alumina-doped yttrium partially stabilized zirconia precursor with 1-5 mol % aluminum and yttrium content of 2-6 mol % suspension slurry is obtained.

The hydrothermal-hydrolysis methods 2: In the first, the 1-5 mol % aluminum hydroxide mixed 0.5-0.6 mol/L zirconium oxychloride solution and 1 mol/L carbonyl two amine with volume ratio of 1:1 were added to the reactor, and the reactor was heated into 150° C. for 2-4 hours, the aluminum and zirconium hydroxide gel was generated. The gel was removed and mixed with the above original reaction liquid with the weight ratio of 1:1, and then was put into the flask equipped with a reflux condenser. Under stirring conditions, the hydrous zirconia sol was obtained by hydrolysis at boiling temperature of 100-150 C; After that 2-6 mol % yttrium nitrate solution was added into the hydrated zirconia sol. With stirring until yttrium nitrate was completely dissolved, the precipitation was gradually hydrolyzed and formed: Finally the precipitate can be separated quickly by centrifuging, filtering in vacuum, and washed with distilled water and ethanol, and dried to obtain alumina-doped yttrium partially stabilized zirconia precursor with yttrium content of 2-6 mol % was obtained; then the alumina-doped yttrium partially stabilized zirconia precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized alumina-doped yttrium partially stabilized zirconia precursor with 1-5 mol % aluminum and yttrium content of 2-6 mol % suspension slurry is obtained.

As a preferred choice, the yttrium source is one of yttrium nitrate and yttrium chloride; the zirconium source is one of zirconium hydroxide, zirconium chloride and zirconium nitrate; and the aluminum source is one of aluminum hydroxide, aluminum chloride and aluminum nitrate.

As a preferred choice, the precipitate is a solution formed by ammonium bicarbonate and ammonium hydroxide with concentration of ammonium bicarbonate is 10-50%. The pore forming additives is a micron-scale pore forming additives or a nano-scale pore forming additives. Micron-scale pore forming additives are selected from polyethylene glycol, nitrocellulose, polyacrylic acid, polypropylene amine, polyethylene, polypropylene, polyvinyl chloride, polybutadiene, polystyrene, polyacrylonitrile, polyphenol, polyformaldehyde, polyamide, polycaprolactam, polyaromatic ether, polyaromatic amide, polyimide carbonate and methyl terephthalate, methyl acrylate, and one or more of above; nano-pore forming additives are selected from carbonyl diamide, ethylene, propylene, vinyl chloride, butadiene, styrene, acrylonitrile, phenol, formaldehyde, amide, caprolactam, aromatic ether, aromatic amide, imide carbonate, ethylene glycol and one or more of above.

The micron-scale pore forming additives is used to form 0.2-0.5 micron pores in the films. Nano-scale pore forming additives is used to form 1-100 nano pores in the films and the linear nano pores with width of 1-10 nanometer and length of 50-500 nanometer and their combination.

As a preferred choice, the biomedical engineering material is one of alumina, zirconia, yttrium partially stabilized zirconia and alumina-doped yttrium partially stabilized zirconia.

As a preferred choice, the content of yttrium in yttrium partially stabilized zirconia is 2-6 mol %, the content of aluminum in alumina-doped yttrium partially stabilized zirconia is 1-5 mol %, and the content of yttrium is 2-6 mol %.

As a preferred choice, the manufacturing method of step (3): the substrates after CAD and CAM are heated at a rate of 1-10 C/s to 120-200° C. for drying of 1-2 hours; and then is coated by an inorganic precursor with or without pore forming additives; or the substrates after CAD and CAM are heated at a rate of 1-10 C/s to 120-200° C. for drying of 1-2 hours, and continues heated at a rate of 10-50 C/s to 700-1100° C. for 1-2 hours; and then is coated by an inorganic precursor with or without pore forming additives. Finally, the substrates with coatings are heated a rate of 1-10° C./s to 1400-1700° C. for sintering of 2-3 hours. The thickness of a single film with nanopore is 0.3-3 micron. For the double coating, the inner layer thickness of microporous film is 0.3-3 micron, and the outer layer thickness of nanoporous film is 0.3-3 micron;

As a preferred choice, in the steps (3) for clean process, SC1 cleaning solution, SC2 cleaning solution, SC3 cleaning solution, acetone, alcohol and distilled water are used for ultrasonic cleaning for 10-30 minutes respectively; the formula of SC1 cleaning solution is: $NH_4OH:H_2O_2:H_2O$ with volume ratio is 1:1-2:5-7, and the cleaning temperature is controlled to 65-80° C. The formula of SC2 cleaning solution is: $HCl:H_2O_2:H_2O$ with volume ratio of 1:1-2:6-8, and cleaning temperature is controlled to 65-80° C. The formula of SC3 cleaning solution is: $H_2SO_4:H_2O_2:H_2O$ volume ratio is 1:1:3, and the cleaning temperature is controlled to 100-130° C.

Organic Precursor Processes:

A nano-oxide ceramic film with biological activity is prepared by the following methods:

(1) The surface structures of biomedical engineering materials are formed by computer-aided design and computer-aided manufacturing. The surface structures can be macro-structure of rough surface, abnormal structure or smooth surface. The designs of surface structures are based on the needs of Biomedical Engineering materials.

(2) The organic precursor coating solutions with or without pore forming additives are prepared. The organic precursor coating solutions are used to form one of the microporous and nanoporous alumina thin film, yttrium partially stabilized zirconia thin film and alumina doped yttrium partially stabilized zirconia thin film.

(3) The organic precursor coating solution was used to coat the surface structure of the substrate after step (1)

treatment, dried and sintered at high temperature, cooled naturally, and then cleaned to obtain a single film with nano-pore, or a double films with the inner layer of micro-pore film and the outer layer of nano-pore film.

As an example, the organic precursor coating solution was used to coat the surface structure of the substrate after step (1) treatment, dried and sintered at high temperature, cooled naturally, and then cleaned to obtain a single film with nano-pore, or a double films with the inner layer of micro-pore film and the outer layer of nano-pore film.

As a preferred choice, a bioactive nanooxide ceramic film is prepared by an organic precursor coating solution such as a sol gel film process: a metal alcohol salt is dissolved into pure ethanol to form a precursor solution with concentration of 0.1-0.5 mole/L, and then the deionized water is added to the precursor solution with stirring evenly, and the mixed solution is obtained. After that, DMF is added to the mixed solution to form a composite solution. The molar ratio in the composite solution is: the amount of the precursor solution: the amount of ethanol:deionized water:DMF=1:1-4:5-10: 0.2-0.4; Finally 1-5 wt % of micro- or nano-pore forming additives is added into the composite solution and stirring for 10-15 minutes and sealed at room temperature for 0.5-2 hours and organic precursor coating solution was obtained. After the organic precursor coating solution is coated on substrates and stayed for 10 s-15 s, the organic precursor coating solution changes into gel film. The gel film is headed at rates of 1-10° C. up to 80-120° C. for 1-2 hours, the dried film is obtained. The above processes can be repeated several times, the target thickness can reach.

As a preferred choice, the precursor materials for forming alumina film are Al-containing metal alkoxide, and the precursor materials for forming yttrium partially stabilized zirconia film are Zr and Y-containing metal alkoxide. The precursor materials for forming alumina-doped yttrium partially stabilized zirconia film are metal alkoxide containing Al, Zr and Y.

As a preferred choice, the organic precursors for the organic compound decomposition film processes are prepared: the 2-ethylhexanoate containing metal ions such as Al, Zr, and Y are dissolved into the mixed solvent of 2-ethylhexanoic acid and methylbenzene to form the precursor solution material with concentration of 0.1-0.5 mole/L. The molar ratio of 2-ethylhexanoic acid to toluene is 1:1-2 in the mixed solvent. Finally the 1-5 wt % of micro- or nano-pore-forming additives are added into the organic precursor solution and stirred for 10-30 minutes at 60-80° C. to form uniform and transparent solution. The organic precursor solution was sealed for 0.5-2 hours at room temperature, and organic precursor coating solution was obtained. After the organic precursor coating solution is coated on substrates and stayed for 1 s-5 s, the organic precursor coating solution changes into gel film. The gel film is headed at 220-250° C. directly for 3-5 minutes, the dried film is obtained. The above processes can be repeated several times, the target thickness can reach.

As a preferred choice, the precursor materials for forming alumina film are 2-ethylhexanoate containing metal ion of Al, and the precursor materials for forming yttrium partially stabilized zirconia film are 2-ethylhexanoate containing metal ions of Zr and Y. The precursor materials for forming alumina-doped yttrium partially stabilized zirconia film are 2-ethylhexanoate containing metal ions of Al, Zr and Y.

As a preferred choice, the pore forming additives are micron-scale pore forming additives or nano-scale pore forming additives. Micron-scale pore forming additives are selected from polyethylene glycol, nitrocellulose, polyacrylic acid, polypropylene amine, polyethylene, polypropylene, polyvinyl chloride, polybutadiene, polystyrene, polyacrylonitrile, polyphenol, polyformaldehyde, polyamide, polycaprolactam, polyaromatic ether, polyaromatic amide, polyimide carbonate and methyl terephthalate, methyl acrylate, and one or more of above; nano-pore forming additives are selected from carbonyl diamide, ethylene, propylene, vinyl chloride, butadiene, styrene, acrylonitrile, phenol, formaldehyde, amide, caprolactam, aromatic ether, aromatic amide, imide carbonate, ethylene glycol and one or more of above.

As a preferred choice, the content of yttrium in yttrium partially stabilized zirconia is 2-6 mol %, the content of aluminum and the content of yttrium in in the alumina-doped yttrium partially stabilized zirconia are 1-5 mol %, and 2-6 mol % respectively.

As a preferred choice, in the steps (3) for clean process, SC1 cleaning, SC2 cleaning, SC3 cleaning, acetone, alcohol and distilled water are used for ultrasonic cleaning for 10-30 minutes respectively; the formula of SC1 cleaning solution is: $NH_4OH:H_2O_2:H_2O$ with volume ratio is 1:1-2:5-7, and the cleaning temperature is at 65-80° C. The formula of SC2 cleaning solution is: $HCl:H_2O_2:H_2O$ with volume ratio of 1:1-2:6-8, and cleaning temperature is at 65-80° C. The formula of SC3 cleaning solution is: $H_2SO_4:H_2O_2:H_2O$ volume ratio is 1:1:3, and the cleaning temperature is at 100-130° C.

As a preferred choice, the thickness of a single film with nanopore is 0.3-3 micron. For the double coating, the inner layer thickness of microporous film is 0.3-3 micron, and the outer layer thickness of nanoporous film is 0.3-3 micron.

As a preferred choice, the biologically active nano-oxide ceramic film is by one of the following processes:

Process 1: The surface structure of biomedical engineering materials is formed by computer-aided design and computer-aided manufacturing; The biomedical engineering materials are heated at a rate of 1-10° C. is up to 120-200° C. and dried for 1-2 hours. After cooling dawn, the organic precursor coating solution is used to coat and bake on the surface of the biomedical engineering materials. Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

Process 2: The surface structure of biomedical engineering materials is formed by computer-aided design and computer-aided manufacturing; The biomedical engineering materials are heated at a rate of 1-10° C./s up to 120-200° C. and dried for 1-2 hours and continue to be heated at a rate of 10-50° C./s up to 700-1100° C. and fried for 1-2 hours. After cooling dawn, the organic precursor coating solution is used to coat and bake on the surface of the biomedical engineering materials. Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

Process 3: The biomedical engineering materials are heated at a rate of 1-10° C./s up to 120-200° C. and dried for 1-2 hours; After cooling dawn, the surface structure of biomedical engineering materials is formed by computer-aided design and computer-aided manufacturing, and then, the organic precursor coating solution is used to coat on the surface of the biomedical engineering materials; after baking, the biomedical engineering materials with coating are heated at a rate of 10-50° C./s up to 700-1100° C. and fried for 1-2 hours. After cooling dawn, the organic precursor coating solution is used to coat and bake again on the surface of the biomedical engineering materials. Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

The nano-oxide ceramic films formed by the invention have grain size of 100-500 nanometers. The materials and products show not only higher strength and toughness, but also good biocompatibility and biological activity.

If the chemically inert ceramic materials or their surfaces have nanostructures and match the size of protein molecules or bone glue molecules, the protein molecules or bone glue molecules will be adsorbed and grow on the nanostructure, which shows good biological activity, it was further found that the hydrophilicity of materials, the adsorption of serum, protein and drugs and the growth factors of the protein molecules or bone glue molecules were determined by nanopore topology and the morphology and structure of water on the inner surface of nanoporous channels. Due to the selective adsorption and proliferation of protein cells on the surface of nanoporous zirconia nanoceramics, the periodontal soft tissue or bone tissue were formed on the surface of the zirconia nanoceramic. Based on the above principles, the invention prepares the biomimetic nanostructured films to greatly improve the biocompatibility and biological activity of zirconia biological materials and products.

Animal experiments show that these bioengineering materials and products with biomimetic micro to nanopore gradient films of the alumina, yttrium partially stabilized zirconia and alumina-doped yttrium partially stabilized zirconia exhibit good biocompatibility and biological activity.

The nano-oxide ceramic films processed by the invention can be either pure nanoporous films, or a double films with an inner micron porous film and outer nanoporous film. The nano-oxide ceramic films prepared by the invention can be used in dental materials, as well as on all artificial bones, including maxillofacial skeleton, skull, hip joint, meniscus, etc.

Simple nanoporous films can cooperate with the surface structures on the substrate made by CAM. For example, a simple nanoporous film coated on the surface structures with micron-scale patterns of a thickness of 0.3-0.5 micron forms a micro to nano gradient structure. On another way, the micro-nano gradient structure can be formed by a double films with an inner micron porous film and outer nanoporous.

The benefits of the present invention are as follows: in order to meet the needs of both the higher strength and toughness, and the better biocompatibility and biological activity for the biomedical engineering materials, the invention prepared the films with biomimetic micro-nano gradient pore structure on the surface of the bioinert medical engineering materials. The micro-nano gradient structure porous thin film materials are also alumina, yttrium stabilized zirconia and yttrium stabilized zirconia doped with alumina. These bioengineering materials and products show a higher strength and toughness and a better biocompatibility and biological activity. These materials and products will be widely used in the field of biomedical engineering.

BRIEF DESCRIPTION OF THE DRAWINGS

FIG. 5A is a morphology with biomimetic nano-pore structure, FIG. 5b is a side-viewing morphology with biomimetic micron-nano gradient pore structure, FIG. 5C is a morphology with biomimetic nano-pore structure, FIG. 5D is morphology with biomimetic single nano-pore, nano-pores, and pores combined linear pore structures.

Figure 1:
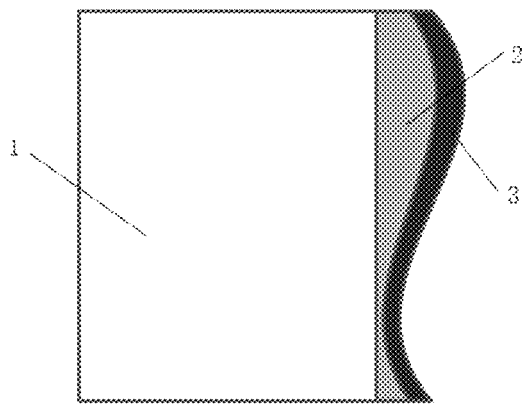
FIG. 1 is biomedical engineering materials and products with a macro structure surface coated by a biomimetic nanopore gradient film.

In the figures: 1. Substrate, 2. Surface structure, 3. Coating, 3.1 coating with micron pore, 3.2 coating with nanopores.

DETAILED DESCRIPTION OF PREFERRED EMBODIMENTS

The technical processes of the present invention is further detailed described.

In the present invention, if it is not specified, the used raw materials and equipment can be purchased from the market or commonly used in the field. The processes in the following embodiments, if it is not specifically described, are conventional methods in the field.

Embodiments

1. Raw Materials, Reagents and Cleaning Processes:

Zirconium hydroxide ($ZrO(OH)_2$-$nH_2O \geq 99\%$), zirconium chloride ($ZrOCl_2 \cdot 8H_2O \geq 99\%$), zirconium nitrate ($Zr(NO_3)_4 \cdot 5H_2O \geq 99\%$) yttrium oxide ($Y_2O_3 \geq 99.99\%$), yttrium nitrate $Y(NO_3)_3 \cdot 6H_2O$, yttrium chloride ($YCl_3 \cdot 6H_2O \geq 99\%$); aluminum hydroxide ($Al(OH)_3 \geq 99\%$), aluminum nitrate ($Al(NO_3)_3 \cdot 9H_2O$), anhydrous alcohol ($C_2H_5OH$) analytical purity; distilled water $H_2O$; ammonia ($NH_3 \cdot H_2O$ analytical purity); sulfuric acid, hydrochloric acid, hydrogen peroxide, deionized water, acetone, alcohol and etc.

The formulation and processes for the three cleaning methods: SC1 cleaning, SC2 cleaning, SC3 cleaning, acetone, alcohol and distilled water are used for ultrasonic cleaning for 10-30 minutes respectively; the formula of SC1 cleaning solution is: $NH_4OH:H_2O_2:H_2O$ with volume ratio is 1:1-2:5-7, and the cleaning temperature is at 65-80° C. The formula of SC2 cleaning solution is: $HCl:H_2O_2:H_2O$ with volume ratio of 1:1-2:6-8, and cleaning temperature is at 65-80° C. The formula of SC3 cleaning solution is: $H_2SO_4:H_2O_2:H_2O$ volume ratio is 1:1:3, and the cleaning temperature is at 100-130° C.

2. The Examples of the Manufacturing Processes for Alumina, Y-Partially Stabilized $ZrO_2$ and Aluminum-Doped Y-Partially Stabilized $ZrO_2$ Powders:

2.1 The Examples of the Manufacturing Processes for Alumina Powders

2.1.1. An Example of the Manufacturing Process of Alumina Powder A:

The aluminum solutions are kinds of aluminum hydroxide suspension, aluminum chloride solution and aluminum nitrate solution, and the precipitate is $NH_4HCO_3$(10-50%)+$NH_3 \cdot H_2O$ solution. In the first, the aluminum solution is slowly dropped into precipitate with stirring strongly to make it fully reaction, aging more than 8-12 hours after reaction, separating rapidly by centrifuging, filtering precipitation in vacuum, washing with distilled water and ethanol, and drying at 100-200° C. for 1-2 hours to obtain alumina powder A

2.1.2. An Example of the Manufacturing Process for Alumina Powder B:

The hydrothermal-hydrolysis method is as follows: In the first, the aluminum hydroxide suspension with concentration of 0.5-1 mol/L is put into the reactor, and the reactor is heated up to 40-60° C. for 2-3 hours, and polyvinyl alcohol with 0.5-1 wt % (the amount of aluminum hydroxide) was added to the reactor and the reactor continues heated to 200-250° C. and kept the pressure at 2-3 MPa with 55-65 hours for hydrothermal-hydrolysis reaction, so that the precipitate can be hydrolyzed gradually; after that the precipitate can be separated quickly by centrifuging, filtering in vacuum, and washing with distilled water and ethanol, and drying at 100-200° C. for 1-2 hours to obtain alumina powder B

2.2. An Example of Manufacturing Process for Y-Partially Stabilized $ZrO_2$ Powder:

2.2.1 The Manufacturing Process of Y Partially Stabilized ZrO 2 Powder a with Y (2-6 Mol %) is as Follows:

Y partially stabilized $ZrO_2$ precipitation is prepared by a reverse dripping method. There is a conical bottle with a magnetic stirrer in a bath reactor having a constant temperature water. The precipitate of $NH_4HCO_3$ (10-50%)+$NH_3 \cdot H_2O$ solution is placed into the conical bottle. Based on the formula of Y partially stabilized $ZrO_2$ powder, the mixed solution has been prepared using one of zirconium hydroxide ($ZrO(OH)_2 \cdot nH_2O$ 99%), zirconium chloride ($ZrOCl_2 \cdot 8H_2O$ 99%), zirconium nitrate ($Zr(NO_3)_4 \cdot 5H_2O$ 99%); and one of yttrium nitrate $Y(NO_3)_3 \cdot 6H_2O$, yttrium chloride ($YCl_3 \cdot 6H_2O$ 99%) The mixed solution is slowly dripping into the precipitate with stirring strongly to make reaction completely. After aging for more than 8-12 hours, the precipitation is quickly separated by centrifuge, filtering in vacuum, washing with distilled water and ethanol, and drying for 1-2 hours at 100-200° C. for 1-2 hours to obtain part Y partially stabilized $ZrO_2$ powder A.

2.2.2. Y(2-6 Mol %) Partially Stabilized $ZrO_2$ Powder C is Fabricated as Follows:

$ZrO(OH)_2 \cdot nH_2O$ (>99%) suspension with concentration of 0.5-1 mol/L of $Zr^{4+}$ is added to a reactor, and yttrium oxide is added to the reactor dividing into three to five times. The reactor is heated to 40-60° C. and keeping for 2-3 hours. After yttrium oxide is dissolved completely, polyvinyl alcohol with 0.5-1 wt % of zirconium hydroxide weight is added, and then heating to 200-250° C. for 55-65 hours for hydrothermal-hydrolysis reaction. The reactor maintains an internal pressure of 2-3 MPa at the same time and to make it hydrolyze and precipitate gradually. The precipitation is separated quickly by centrifuging, filtering by vacuum, washing with distilled water and ethanol, and drying for 1-2 hours at 100-200° C. The Y stable $ZrO_2$ powder C is obtained.

2.2.3. The example of manufacturing process for Y (2-6 mol %) partially stabilized $ZrO_2$ powder D is the same with 2.2.2 Y partially stabilized $ZrO_2$ powder C except of that the mixture with weight ratio 1:1 of polyacrylic acid and polyvinyl alcohol is used instead of polyvinyl alcohol.

2.2.4. The Example of Manufacturing Process for Y (2-6 Mol %) Partially Stabilized $ZrO_2$ Powder E is as Follows:

The zirconium oxychloride ($ZrOCl_2 \cdot 8H_2O$ (>99%) solution with concentration of 0.5-1 mol/L of $Zr^{4+}$ and carbonyl two amine $(NH_2)_2CO$ with concentration of 1 mol/L is added into a reactor, and heating the reactor to 150° C. for hydrothermal reaction and holding 2-4 hours to produce gel. The original reaction solution is added into the gel with ratio of 1:1, stirring in the flask equipped with a reflux condenser, and the hydrolysis continues at 100-150° C. The conversion rate of hydrated $Zr(OH)_4$ solution reaches at 99%. Adding yttrium nitrate to the hydrated $Zr(OH)_4$ solution with stirring, and then yttrium nitrate dissolving completely, and then the Y (2-6 mol %) partially stabilized $ZrO_2$ solution is hydrolyzed and precipitated gradually. The precipitation is separated quickly by centrifuging, filtering by vacuum, washing with distilled water and ethanol, and drying for 1-2 hours at 100-200° C. to obtain Y partially stabilized $ZrO_2$ powders E.

2.3. An Example of Manufacturing Process for Al Doped Y Partially Stabilized $Zro_2$ Powder:

The example of manufacturing process of Al (1-5 mol %) doped Y (2-6 mol %) partially stabilized $ZrO_2$ powder F is as follows: Al doped Y partially stabilized $ZrO_2$ precipitation is prepared by a reverse dripping method. There is a conical bottle with a magnetic stirrer in a bath reactor having a constant temperature water. The precipitate of $NH_4HCO_3$ (10-50%)+$NH_3 \cdot H_2O$ solution is placed into the conical bottle. Based on the formula of Al doped Y partially stabilized $ZrO_2$ powder, the mixed solution has been prepared using one of zirconium hydroxide ($ZrO(OH)_2 \cdot nH_2O$ 99%), zirconium chloride ($ZrOCl_2 \cdot 8H_2O$ 99%), zirconium nitrate ($Zr(NO_3)_4 \cdot 5H_2O$ 99%); and one of yttrium nitrate $Y(NO_3)_3 \cdot 6H_2O$, yttrium chloride ($YCl_3 \cdot 6H_2O$ 99%) and one of aluminum hydroxide ($Al(OH)_3 \geq 99\%$), Aluminum nitrate ($Al(NO_3)_3 \cdot 9H_2O$ 99%). The mixed solution is slowly dripping into the precipitate with stirring strongly to make reaction completely. After aging for more than 8-12 hours, the precipitation is quickly separated by centrifuge, filtering in vacuum, washing with distilled water and ethanol, and drying for 1-2 hours at 100-200° C. for 1-2 hours to obtain Al doped Y partially stabilized. $ZrO_2$ powder F.

2.3.2. An Example of Manufacturing Process for Al (1-5 Mol %) Doped Y (2-6 Mol %) Partially Stable ZrO 2 Powder H is as Follows:

$ZrO(OH)_2.nH_2O$ (>99%) suspension and $Al(OH)_3$ (99%) with concentration of 0.5-1 mol/L of $Zr^{4+}$ are added to a reactor, and yttrium oxide is added to the reactor dividing into three to five times. The reactor is heated to 40-60° C. and keeping for 2-3 hours. After yttrium oxide is dissolved completely, polyvinyl alcohol with 0.5-1 wt % of zirconium hydroxide weight is added, and then heating to 200-250° C. for 55-65 hours for hydrothermal-hydrolysis reaction. The reactor maintains an internal pressure of 2-3 MPa at the same time and to make it hydrolyze and precipitate gradually. The precipitation is separated quickly by centrifuging, filtering by vacuum, washing with distilled water and ethanol, and drying for 1-2 hours at 100-200° C. The Al doped Y stable $ZrO_2$ powder H is obtained.

2.3.3. The example of manufacturing process for Al (1-5 mol %) doped Y (2-6 mol %) partially stabilized $ZrO_2$ powder I is the same with 2.3.2 Al doped Y partially stabilized $ZrO_2$ powder H except of that the mixture with weight ratio 1:1 of polyacrylic acid and polyvinyl alcohol is used instead of polyvinyl alcohol.

2.3.4. The Example of Manufacturing Process for Al (1-5 Mol %) Doped Y (2-6 Mol %) Partially Stabilized $ZrO_2$ Powder J is as Follows:

The zirconium oxychloride ($ZrOCl_2.8H_2O$ (>99%) solution and $Al(OH)_3$ (99%) with concentration of 0.5-1 mol/L of $Zr^{4+}$ and $Al^{3+}$ and carbonyl two amine $(NH)_2CO$ with concentration of is added into a reactor, and heating the reactor to 150° C. for hydrothermal reaction and holding 2-4 hours to produce gel. The original reaction solution is added into the gel with ratio of 1:1, stirring in the flask equipped with a reflux condenser, and the hydrolysis continues at 100-150° C. The conversion rate of hydrated $Zr(OH)_4$ and $Al(OH)_3$ solution reaches at 99%. Adding yttrium nitrate to the hydrated $Zr(OH)_4$ and $Al(OH)_3$ mixed solution with stirring, and then yttrium nitrate dissolving completely, and then the Al (1-5 mol %) doped Y (2-6 mol %) partially stabilized $ZrO_2$ solution is hydrolyzed and precipitated gradually. The precipitation is separated quickly by centrifuging, filtering by vacuum, washing with distilled water and ethanol, and drying for 1-2 hours at 100-200° C. to obtain Al (1-5 mol %) doped Y partially stabilized $ZrO_2$ powders E.

Inorganic Process:

3. Examples of Manufacturing Process for Coating Suspension Slurry (Inorganic Precursor Coating Solution):

3.1. Examples of Manufacturing Process for Alumina Suspension Slurry 3.1.1 An Example of Manufacturing Process for Aluminum Oxide Suspension Slurry A The liquid phase co-precipitation method is as follows: The aluminum solutions are kinds of aluminum hydroxide suspension, aluminum chloride solution and aluminum nitrate solution, and the precipitate is ammonium hydroxide. In the first, the precipitate is slowly dropped into aluminum solution, stirred strongly to make it fully react, aged more than 8-12 hours after reaction, separated rapidly by centrifuging, filtering precipitation in vacuum, washed with distilled water and ethanol, and dried to obtain alumina precursor; and then the alumina precursor was made into slurry with 2-15 vol % of solid phase content by mixing 1-3 wt % of dispersant such as propanolamine and deionized water; after that adjusting PH of the slurry to 3-6, and put into ball milling such as in planetary mill for 10-30 h, finally adjusting PH of the slurry to 8-10 and adding and mixing 1-5 wt % of pore forming additives (such as PEG1000, nitrocellulose, polyacrylic acid, polypropylene glycol amine, polyethylene, polypropylene, polyvinyl chloride, polybutadiene, polystyrene and polypropylene). Polyacrylonitrile, polyphenol, polyformaldehyde, polyamide, polycaprolactam, polyaromatic ether, polyaromatic amide, polyimide carbonate, methyl methacrylate terephthalate, etc.) based on the weight of alumina to obtain nano-sized alumina suspension slurry.

3.1.2 An Example of Manufacturing Process of Aluminum Oxide Suspension Slurry B

The hydrothermal-hydrolysis method is as follows: In the first, the aluminum hydroxide suspension with concentration of 0.5-1 mol/L is put into the reactor, and heated the reactor to 40-60° C. for 2-3 hours, and then added 0.5-1 wt % of dispersant such as $CA(C_6H_8O_7.H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain alumina precursor; then the alumina precursor is mixed with 1-3 wt % dispersant such as $CA(C_6H_8O_7.H_2O)$ and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives such as $NH_2CO$, ethylene, acrylic acid, phenol, formaldehyde, amide, caprolactam, aromatic ether, aromatic amide, imide carbonate, ethylene glycol, propanolamine and their combination, the nano-sized alumina suspension slurry is obtained.

3.2. The Examples of Manufacturing Processes for Y Stabilized $ZrO_2$ Suspension Slurry A:

An example of manufacturing process for Y partially stabilized $ZrO_2$ suspension slurry A is as follows: The liquid phase co-precipitation method is as follows: The zirconium solutions are kinds of zirconium hydroxide suspension, zirconium chloride solution and zirconium nitrate solution, and the yttrium solutions are kinds of yttrium hydroxide suspension, yttrium chloride solution and yttrium nitrate solution, and the precipitate is ammonium hydroxide. In the first, the precipitate is slowly dropped into mixed zirconium with 2-6 mol % of yttrium content solution, stirred strongly to make it fully react, aged more than 8-12 hours after reaction, separated rapidly by centrifuging, filtering precipitation in vacuum, washed with distilled water and ethanol, and dried to obtain yttrium partially stabilized zirconia precursor, and then the yttrium partially stabilized zirconia precursor was made into slurry with 2-15 vol % of solid phase content by mixing 1-3 wt % of dispersant such as propanolamine and deionized water; after adjusting PH of the slurry to 3-6, and put into ball milling such as in planetary mill for 10-30 h, finally adjusting PH of the slurry to 8-10 and adding and mixing 1-5 wt % of pore forming additives such as polyvinyl alcohol and polyethylene glycol (PEG1000) based on the weight of yttrium partially stabilized zirconia precursor to obtain nano-sized yttrium partially stabilized zirconia suspension slurry.

3.2.2. Y (2-6 Mol %) Partially Stabilized ZrO 2 Suspension Slurry B was Fabricated as Follows:

Y partially stabilized. $ZrO_2$ precipitation is prepared by a reverse dripping method. There is a conical bottle with a magnetic stirrer in a bath reactor having a constant temperature water. The precipitate of $NH_4HCO_3$ (10-50%)+ $NH_3.H_2O$ solution is placed into the conical bottle. Based on the formula of Y partially stabilized $ZrO_2$ powder, the mixed solution has been prepared using one of zirconium hydroxide ($ZrO(OH)_2.nH_2O$ 99%), zirconium chloride ($ZrOCl_2.8H_2O$ 99%), zirconium nitrate ($Zr(NO_3)_4.5H_2O$ 99%); and one of yttrium nitrate $Y(NO_3)_3. 6H_2O$, yttrium chloride ($YCl_3. 6H_2O$ 99%). The mixed solution is slowly dripping into the precipitate with stirring strongly to make reaction completely. After aging for more than 8-12 hours, the precipitation is quickly separated by centrifuge, filtering in vacuum, washing with distilled water and ethanol to obtain Y partially stabilized $ZrO_2$ precursor, and then the Y partially stabilized $ZrO_2$ precursor is made into slurry with 2-15 vol % of solid phase content by mixing 1-3 wt % of dispersant such as citric acid and deionized water; after that adjusting PH of the slurry to 3-6, and put into ball milling such as in planetary mill for 10-30 h, finally adjusting PH of the slurry to 8-10 and adding and mixing 1-5 wt % of pore forming additives such as nitrocellulose based on the weight of alumina to obtain nano-sized Y partially stabilized. $ZrO_2$ precursor suspension slurry B.

3.2.3. An Example of Manufacturing Process for Y (2-6 Mol %) Partially Stabilized $ZrO_2$ Suspension Slurry C is as Follows:

The hydrothermal-hydrolysis methods 1: In the first, the Zirconium hydroxide suspension with concentration of 0.5-1 mol/L is put into the reactor, then yttrium oxide was added and mixed into the reactor 3-5 times respectively, and heated the reactor to 40-60° C. for 2-3 hours, and then added 0.5-1 wt % of dispersant such as $CA(C_6H_8O_7.H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain yttrium-stabilized zirconia precursor with yttrium content of 2-6 mol % was obtained; then the yttrium-stabilized zirconia precursor is mixed with 1-3 wt % dispersant such as propanolamine and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, such as polyethylene glycol, nitrocellulose, polyacrylic acid, polypropylene amine, polyethylene, polypropylene, polyvinyl chloride, polybutadiene, polystyrene, polyacrylonitrile, polyphenol, polyformaldehyde, polyamide, polycaprolactam, polyaromatic ether, polyaromatic amide, polyimide carbonate and methyl terephthalate, methyl acrylate, and one or more of above; nano-pore forming additives are selected from carbonyl diamide, ethylene, propylene, vinyl chloride, butadiene, styrene, acrylonitrile, phenol, formaldehyde, amide, caprolactam, aromatic ether, aromatic amide, imide carbonate, ethylene glycol and one or more of above, the nano-sized yttrium-stabilized zirconia precursor with yttrium content of 2-6 mol % suspension slurry C is obtained.

3.2.4. An Example of Manufacturing Process for Y (2-6 Mol %) Partially Stabilized $ZrO_2$ Suspension Slurry D is as Follows:

The hydrothermal-hydrolysis methods 2: In the first, the Zirconium hydroxide suspension with concentration of 0.5-1 mol/L is put into the reactor, then yttrium oxide was added and mixed into the reactor 3-5 times respectively, and heated the reactor to 40-60° C. for 2-3 hours, and then added 0.5-1 wt % of dispersant such as the mixture of 0.5-1 wt % of polyacrylic acid and polyvinyl alcohol with ratio of 1:1 according to the amount of zirconium hydroxide, and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain yttrium-stabilized zirconia precursor with yttrium content of 2-6 mol % was obtained; then the yttrium-stabilized zirconia precursor is mixed with 1-3 wt % dispersant such as propanolamine and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized yttrium-stabilized zirconia precursor with yttrium content of 2-6 mol % suspension slurry D is obtained.

3.2.5. An Example of Manufacturing Process for Y (2-6 Mol %) Partially Stabilized $ZrO_2$ Suspensions Slurry E was as Follows:

The hydrothermal-hydrolysis methods 3: In the first, the 0.5-0.6 mol/L zirconium oxychloride solution and 1 mol/L carbonyl two amine with volume ratio of 1:1 were added to the reactor, and the reactor was heated into 150° C. for 2-4 hours, the zirconium hydroxide gel was generated. The gel was removed and mixed with the above original reaction liquid with the weight ratio of 1:1, and then was put into the flask equipped with a reflux condenser. Under stirring conditions, the hydrous zirconia sol was obtained by hydrolysis at boiling temperature of 100-150 C; After that 2-6 mol % yttrium nitrate solution was added into the hydrated zirconia sol. With stirring until yttrium nitrate was completely dissolved, the precipitation was gradually hydrolyzed and formed; Finally the precipitate can be separated quickly by centrifuging, filtering in vacuum, and washed with distilled water and ethanol, and dried to obtain yttrium-stabilized zirconia precursor with yttrium content of 2-6 mol % was obtained; then the yttrium-stabilized zirconia precursor is mixed with 1-3 wt % dispersant such as triethanolamine and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized yttrium-stabilized zirconia precursor with yttrium content of 2-6 mol % suspension slurry E is obtained.

3.3. An Example of Manufacturing Process for Al Doped Y Partially Stabilized $ZrO_2$ Suspension Slurry 3.3.1. An Example of Manufacturing Process for Al Doped Y Partially Stabilized $ZrO_2$ Suspension Slurry F is as Follows:

The liquid phase co-precipitation method is as follows: The zirconium solutions are kinds of zirconium hydroxide suspension, zirconium chloride solution and zirconium nitrate solution, and the yttrium solutions are kinds of yttrium hydroxide suspension, yttrium chloride solution and yttrium nitrate solution. The aluminum solutions are kinds of aluminum hydroxide suspension, aluminum chloride solution and aluminum nitrate solution, and the precipitate is ammonium hydroxide. In the first, the precipitate is slowly dropped into mixed 1-5 mol % aluminum and zirconium with 2-6 mol % of yttrium content solution, stirred strongly to make it fully react, aged more than 8-12 hours after reaction, separated rapidly by centrifuging, filtering precipitation in vacuum, washed with distilled water and ethanol, and dried to obtain alumina-doped yttrium partially stabilized zirconia precursor; and then the alumina-doped yttrium partially stabilized zirconia precursor was made into slurry with 2-15 vol % of solid phase content by mixing 1-3 wt % of dispersant such as propanolamine and deionized water; after adjusting PH of the slurry to 3-6, and put into ball milling such as in planetary mill for 10-30 h, finally adjusting PH of the slurry to 8-10 and adding and mixing 1-5 wt % of pore forming additives based on the weight of alumina-doped yttrium partially stabilized zirconia precursor to obtain nano-sized alumina-doped yttrium partially stabilized zirconia suspension slurry F.

3.3.2. An Example of Manufacturing Process for Al (1-5 Mol %) Doped Y (2-6 Mol %) Partially Stabilized $ZrO_2$ Suspension Slurry G is as Follows:

The hydrothermal-hydrolysis methods 1: In the first, the 1-5 mol % aluminum mixed zirconium hydroxide suspension with concentration of 0.5-1 mol/L is put into the reactor, then yttrium oxide was added and mixed into the reactor diving into 3-5 times, and heated the reactor to 40-60° C. for 2-3 hours, and then added 0.5-1 wt % of dispersant such as $CA(C_6H_8O_7 \cdot H_2O)$ and heated to 200-250° C. and kept the pressure at 2-3 MPa with 55-65 hours for hydrothermal-hydrolysis reaction, so that the precipitate can be hydrolyzed gradually; then the precipitate can be separated quickly by centrifuging, filtering in vacuum, and washed with distilled water and ethanol, and dried to obtain alumina-doped yttrium partially stabilized zirconia precursor with 1-5 mol % aluminum and yttrium content of 2-6 mol % was obtained; then the alumina-doped yttrium partially stabilized zirconia precursor is mixed with 1-3 wt % dispersant such as propanolamine and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized alumina-doped yttrium partially stabilized zirconia precursor with 1-5 mol % aluminum and yttrium content of 2-6 mol % suspension slurry G is obtained.

3.3.3. An Example of Manufacturing Process for Al (1-5 Mol %) Doped Y (2-6 Mol %) Partially Stable $ZrO_2$ Slurry Suspension G is as Follows:

The hydrothermal-hydrolysis methods 2: In the first, the 1-5 mol % aluminum hydroxide mixed 0.5-0.6 mol/L zirconium oxychloride solution and 1 mol/L carbonyl two amine with volume ratio of 1:1 were added to the reactor, and the reactor was heated into 150° C. for 2-4 hours, the aluminum and zirconium hydroxide gel was generated. The gel was removed and mixed with the above original reaction liquid with the weight ratio of 1:1, and then was put into the flask equipped with a reflux condenser. Under stirring conditions, the hydrous zirconia sol was obtained by hydrolysis at boiling temperature of 100-150 C; After that 2-6 mol % yttrium nitrate solution was added into the hydrated zirconia sol. With stirring until yttrium nitrate was completely dissolved, the precipitation was gradually hydrolyzed and formed; Finally the precipitate can be separated quickly by centrifuging, filtering in vacuum, and washed with distilled water and ethanol, and dried to obtain alumina-doped yttrium partially stabilized zirconia precursor with yttrium content of 2-6 mol % was obtained; then the alumina-doped yttrium partially stabilized zirconia precursor is mixed with 1-3 wt % dispersant such as triethanolamine and citric acid and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized alumina-doped yttrium partially stabilized zirconia precursor with 1-5 mol % aluminum and yttrium content of 2-6 mol % suspension slurry H is obtained.

4. The Examples of Fabrication Methods for Bioengineering Materials with Bioactive Films Such as Nano-Alumina, Yttrium Partially Stabilized Zirconia and Aluminay Doped Yttrium Partially Stabilized Zirconia 4.1 The Examples of Manufacturing Methods for Bioengineering Materials with Bioactive Nano-Gradient Alumina Films 4.1.1 An Example 1 of Manufacturing Process for Bioengineering Materials with Micron-Scale Macrostructure and Biomimetic Nano-Pore Gradient Alumina Film Structure:

Aluminum oxide, yttrium partially stabilized zirconia and alumina doped yttrium partially stabilized zirconia powders are mixed with 1-3 wt % dispersant such as citric acid solution and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, the nano-sized aluminum oxide, yttrium partially stabilized zirconia and alumina doped yttrium partially stabilized zirconia slurrys are obtained. The substrates of the nano-sized aluminum oxide, yttrium partially stabilized zirconia and alumina doped yttrium partially stabilized zirconia have been fabricated by forming methods. The surface structure of the biomedical engineering materials is formed by computer-aided design and computer-aided manufacturing: The biomedical engineering materials are heated at a rate of 1-10° C./s up to 120-200° C. and dried for 1-2 hours. After cooling dawn, the alumina coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

4.1.2 An Example 2 of Manufacture Process for Bioengineering Materials with Micron-Scale Macro-Structure and Biomimetic Nano Gradient Alumina Film Structure Aluminum oxide, yttrium partially stabilized zirconia and alumina doped yttrium partially stabilized zirconia powders are mixed with 1-3 wt % dispersant such as propanolamine solution and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, such as $CA(C_6H_8O_7 \cdot H_2O)$, the nano-sized aluminum oxide, yttrium partially stabilized zirconia and alumina doped yttrium partially stabilized zirconia slurrys are obtained. The substrates of the nano-sized aluminum oxide, yttrium partially stabilized zirconia and alumina doped yttrium partially stabilized zirconia have been fabricated by forming methods. The surface structure of the biomedical engineering materials is formed by computer-aided design and computer-aided manufacturing; The biomedical engineering materials are heated at a rate of 1-10° C./s up to 120-200° C. and dried for 1-2 hours, and continues heated at a rate of 10-50° C./s up to 700-1100° C. for pre-sintering of 1-2 hours. After cooling dawn, the substrates with coatings cleaned by water with ultrasonic wave, dry, and clean with acetone, then the alumina coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

4.1.3 An Example 3 of Manufacture Process for Bioengineering Materials with Micron-Scale and Biomimetic Nano Gradient Alumina Film Structure Aluminum oxide, yttrium partially stabilized zirconia and alumina doped yttrium partially stabilized zirconia powders are mixed with 1-3 wt % dispersant such as propanolamine solution and the deionized water to form a slurry with 2-15 vol % of solid content. After adjusting the pH to 3-6, the slurry is put into the ball milling such as in planetary mill for 10-30 hours, and adjusted the slurry pH to 8-10, and added and mixed 1-5 wt % of a pore forming additives, such as $CA(C_6H_8O_7 \cdot H_2O)$ the nano-sized aluminum oxide, yttrium partially stabilized zirconia and alumina doped yttrium partially stabilized zirconia slurrys are obtained. The substrates of the nano-sized aluminum oxide, yttrium partially stabilized zirconia and alumina doped yttrium partially stabilized zirconia have been fabricated by forming methods. The surface structure of the biomedical engineering materials is formed by computer-aided design and computer-aided manufacturing; The biomedical engineering materials are heated at a rate of 1-10° C./s up to 120-200° C. and dried for 1-2 hours. After cooling dawn, the alumina coating solution with micron-scale pore forming additives is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; then the substrate with coatings is heated at a rate of 1-10 C/s to 120-200° C. for drying of 1-2 hours; and continues increase the temperature at a rate of 10-50° C./s to 700-1100° C. for pre-sintering of 1-2 hours; After cooling dawn, the substrates with coatings cleaned by water with ultrasonic wave, dry, and clean with acetone, then the alumina coating solution with nano-scale pore forming additives is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Finally the substrates with coatings is increased at a rate of 1-10° C./s up to 1400-1500° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively.

4.2 The Examples of Manufacture Process for Bioengineering Materials with Micron-Scale and Biomimetic Nano Gradient Yttrium Partially Stabilized Zirconia Film.

4.2.1 An Example 1 of Manufacture Process for Bioengineering Materials with Micron-Scale and Biomimetic Nano Gradient Yttrium Partially Stabilized Zirconia Film.

FIG. 1 to 5 show the structures and compositions of bioengineering materials and products with micron-scale macrostructure and biomimetic nano-gradient yttrium partially stabilized zirconia film.

The surface structure of the biomedical engineering materials is formed by computer-aided design and computer-aided manufacturing; The biomedical engineering materials are heated at a rate of 1-10° C./s up to 120-200° C. and dried for 1-2 hours. After cooling dawn, the yttrium partially stabilized zirconia coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Finally the substrates with coatings is increased at a rate of 1-10° C./s up to 1400-1500° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products with micron-scale macrostructure and biomimetic nano-gradient yttrium partially stabilized zirconia film have been fabricated.

4.2.2 An Example 2 of Manufacture Process for Bioengineering Materials with Micron-Scale and Biomimetic Nano Gradient Yttrium Partially Stabilized Zirconia Film.

The surface structure of the biomedical engineering materials is formed by computer-aided design and computer-aided manufacturing; The biomedical engineering materials are heated at a rate of 1-10° C./s up to 120-200° C. and dried for 1-2 hours and continues heated at a rate of 10-50° C./s up to 700-1100° C. for pre-sintering of 1-2 hours. After cooling dawn, the substrates with coatings cleaned by water with ultrasonic wave, dry, and clean with acetone, then the yttrium partially stabilized zirconia coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products with micron-scale macrostructure and biomimetic nano-gradient yttrium partially stabilized zirconia film have been fabricated.

4.2.3 An Example 3 of Manufacture Process for Bioengineering Materials with Micron-Scale and Biomimetic Nano Gradient Yttrium Partially Stabilized Zirconia Film.

The biomedical engineering materials are heated at a rate of 1-10° C./s up to 120-200° C. and dried for 1-2 hours, and continues heated at a rate of 1-10° C./s up to 600° C. and kept for 1-2 hours, and then heated at a rate of 10-50° C./s up to 700-1100° C. for pre-sintering of 1-2 hours. After cooling dawn, the surface structure with deeps of 0.3-0.5 micron structure of the biomedical engineering materials is formed by computer-aided design and computer-aided manufacturing; the substrates is cleaned by water with ultrasonic wave, dry, and clean with acetone, then the yttrium partially stabilized zirconia coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products with micron-scale macrostructure and biomimetic nano-gradient yttrium partially stabilized zirconia film have been fabricated.

4.2.4 An Example 4 of Manufacture Process for Bioengineering Materials with Micron-Scale and Biomimetic Nano Gradient Al Doped Yttrium Partially Stabilized Zirconia Film.

The surface structure with deeps of 0.3-0.5 micron structure of the biomedical engineering materials is formed by computer-aided design and computer-aided manufacturing; The biomedical engineering materials are heated at a rate of 1-10° C./s up to 120-200° C. and dried for 1-2 hours, and continues heated at a rate of 1-10° C./s up to 600° C. and kept for 0.5-1 hours, and then heated at a rate of 10-50° C./s up to 700-1100° C. for pre-sintering of 1-2 hours. After cooling dawn, the substrates is cleaned by water with ultrasonic wave, dry, and clean with acetone, then the Al doped yttrium partially stabilized zirconia coating solution is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products with micron-scale macrostructure and biomimetic nano-gradient Al doped yttrium partially stabilized zirconia film have been fabricated.

4.2.5 An Example 5 of Manufacture Process for Bioengineering Materials with Micron-Scale and Biomimetic Nano Gradient Al Doped Yttrium Partially Stabilized Zirconia Film.

In this example, the yttrium partially stabilized zirconia suspension slurry in the example of 4.2.3 is replaced by the alumina doped yttrium partially stabilized zirconia suspension slurry, and the others are the same as 4.2.3.

4.2.6 An Example 6 of Manufacture Process for Bioengineering Materials with Micron-Scale and Biomimetic Nano Gradient Al Doped Yttrium Partially Stabilized Zirconia Film.

In this example, the yttrium partially stabilized zirconia suspension slurry in the example of 4.2.1 is replaced by the alumina doped yttrium partially stabilized zirconia suspension slurry, and the others are the same as 4.2.3.

4.2.7 An Example 7 of Manufacture Process for a Smooth Surface Structure of Bioengineering Materials Coated by a Micron-Scale and Biomimetic Nano Gradient Yttrium Partially Stabilized Zirconia Film.

Figure 2:
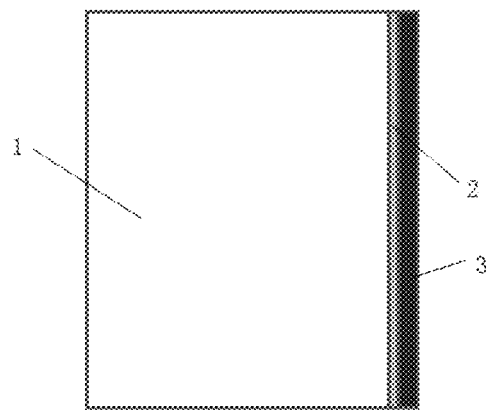
FIG. 2 is biomedical engineering materials and products with a smooth surface coated by a biomimetic nanopore gradient film.

FIG. 2 shows the smooth surface structure and composition of bioengineering materials and products coated by biomimetic nano-gradient yttrium partially stabilized zirconia film.

The difference between this example and 4.2.1 is that the required structure on the bioengineering materials is formed by computer aided design (CAD) and computer aided processing (CAM). The others are the same as 4.2.1.

4.2.8 An Example 8 of Manufacture Process for Bioengineering Materials Smooth Surface Coated by a Micron-Scale and Biomimetic Nano Gradient Al Doped Yttrium Partially Stabilized Zirconia Film.

FIG. 2 shows a smooth surface structure and composition of bioengineering materials coated by biomimetic nano-pore gradient alumina doped yttrium partially stabilized zirconia film.

In this example, the yttrium partially stabilized zirconia suspension slurry in 4.2.7 is replaced by the alumina doped yttrium partially stabilized zirconia suspension slurry, and the others are the same as 4.2.7.

4.2.9 An Example 9 of Manufacture Process for a Smooth Surface Structure of Bioengineering Materials Coated by a Micron-Scale and Biomimetic Nano Gradient Yttrium Partially Stabilized Zirconia Film.

The difference between this example and 4.2.2 is that the required structure on the bioengineering materials is formed by computer aided design (CAD) and computer aided processing (CAM). The others are the same as 4.2.2.

4.2.10 An Example 10 of Manufacture Process for a Profiled Surface Structure of Bioengineering Materials Coated by a Micron-Scale and Biomimetic Nano Pore Gradient Yttrium Partially Stabilized Zirconia Film.

Figure 3:
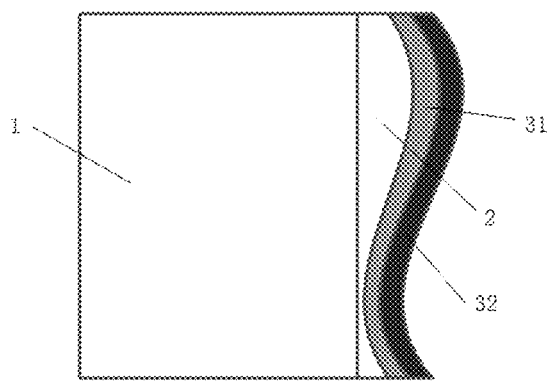
FIG. 3 is bioengineering materials and products with a profiled structure coated by a biomimetic micron-nanopore gradient film.

FIG. 3 shows bioengineering materials and products with profiled surface structure and composition coated by a biomimetic micro-nano pore gradient yttrium partially stabilized zirconia film.

The profiled surface structure of the biomedical engineering materials is formed by computer-aided design and computer-aided manufacturing; The biomedical engineering materials are heated at a rate of 1-10° C./s up to 120-200° C. and dried for 1-2 hours. After cooling dawn, the yttrium partially stabilized zirconia coating solution with 0.2-0.5 micron micron-scale pore forming additives is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; then the substrate with coatings is heated at a rate of 1-10 C/s to 120-200° C. for drying of 1-2 hours; and continues increase the temperature at a rate of 10-50° C./s to 700-1100° C. for pre-sintering of 1-2 hours; After cooling dawn, the substrates with coatings cleaned by water with ultrasonic wave, dry, and clean with acetone, then the yttrium partially stabilized zirconia coating solution with 1-100 nm or diameter of 1-10 nm with length of 50-500 nm nano-scale pore forming additives is used to coat on the surface of the biomedical engineering materials. The substrates with coating is heated at a rate of 1-10 C/s to 120-200° C. for drying of 1-2 hours; and repeating the above steps, the more coatings with thickness of 0.3-3 microns are obtained; After that the substrates with coatings is increased at a rate of 1-10° C./s up to 1400-1500° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products with profiled surface structure and composition coated by a biomimetic micro-nano pore gradient yttrium partially stabilized zirconia film have been fabricated.

4.2.11 An Example 11 of Manufacturing Process for Bioengineering Materials and Products with Profiled Structure Coated by Biomimetic Micro-Nano Pore Gradient Alumina Doped Yttrium Partially Stabilized Zirconia Film.

In this example, the yttrium partially stabilized zirconia suspension slurry in 4.2.10 is replaced by the alumina doped yttrium partially stabilized zirconia suspension slurry, and the others are the same as 4.2.10.

4.2.12 An Example 12 of Manufacturing Process for Bioengineering Materials and Products with Smooth Surface Structure Coated by Biomimetic Micro-Nano Pore Gradient Alumina Doped Yttrium Partially Stabilized Zirconia Film.

The difference between this example and 4.2.1.1 is that the required smooth surface structure bioengineering materials and products is formed by computer aided design (CAD) and computer aided processing (CAM). The others are the same as 4.2.11.

Organic Process:

5. The Examples of Preparation Processes for Alumina, Yttrium Partially Stabilized Zirconia and Alumina Doped Yttrium Partially Stabilized Zirconia Organic Precursor Coating Solution.

Micron pore-forming additives are polymer materials with different molecular weight and different organic groups, such as polyethylene glycol (PEG1000), nitrocellulose, polyacrylic acid, polyvinyl alcohol, polypropanolamine, polyethylene, polypropylene, polyvinyl chloride, polybutadiene, polystyrene, polyacrylonitrile, polyphenol and polyformaldehyde. Polyamide, polycaprolactam, polyaromatic ether, polyaromatic amide, polyimide carbonate, methyl methacrylate terephthalate and their combination are used to form 0.2-0.5 micron pore structure. Nanopore-forming additives are polymer materials with smaller molecular weight and smaller organic groups, such as carbamide, propanolamine, citric acid, ethylene, propylene, vinyl chloride, butadiene, styrene, acrylonitrile, phenol, formaldehyde, amide, caprolactam, aromatic ether, aromatic amide, imide carbonate, ethylene glycol, and their combinations are used to form 1-100 nanoporous structures and linear structures with diameters of 1-10 nm and lengths of 50-500 nm which match the size of protein molecules or bone glue elements.

5.1 Alumina Organic Precursor Coating Solution 5.1.1 An Example of Alumina Organic Precursor Coating Solution A A metal alcohol salts containing metal ions Al are selected as precursor materials such as $Al(OC_3H_7)_3$. The precursor material $Al(OC_3H_7)_3$ is dissolved in anhydrous ethanol to form a precursor solution with a concentration of 0.1-0.5 mole/L. Then the deionized water with ethanol solution of is added to the precursor solution with stirring, and the mixed solution is obtained. Then DMF is added into the mixed solution to form a composite solution. The molar ratio of components in the composite solution is as follows: the amount of precursor solution: the amount of ethanol in the deionized water solution: the amount of deionized water: the amount of DMF=1:1-4:5-10:0.2-0.4; after that 1-5 wt % of micrometer or nanopore forming additives of the precursor material is added to the composite solution with stirring for 10-15 minutes. Finally the composite solution has been sealed and parked at room temperature for 0.5-2 hours. The precursor composite solution for aluminum oxide film with micron or nano-pore additives is obtained 5.1.2 An example of alumina organic precursor coating solution B The precursor material containing metal ion Al such as $Al(C_7H_{15}COO)_3$ is selected as the precursor material. The precursor material of $Al(C_7H_{15}COO)_3$ is dissolved in the solvent of 2-ethylhexanoic acid and toluene to prepare the precursor solution with the concentration of 0.1-0.5 mole/L, in which the molar ratio of 2-ethylhexanoic acid to toluene was 1:1-2. Adding 1-5 wt % of micrometer or nanometer pore-forming additives into the precursor solution with stirring for 10-30 minutes at 60-80° C. to form uniform and transparent organic precursor solution. After that the organic precursor solution has been sealed for 0.5-2 hours at room temperature, the precursor composite solution with the micrometer or nanometer pore additives for making alumina film was obtained.

5.2 The examples of manufacturing process for yttrium partially stabilized zirconia organic precursor coating solution 5.2.1 An example of manufacturing process for yttrium partially stabilized zirconia organic precursor coating solution A The precursor materials containing metal ions Zr and Y such as $Y(OC_3H_7)_3$ and $Zr(OC_3H_7)_4$ are selected as precursor materials. The precursor materials of $Y(OC_3H_7)_3$ and $Zr(OC_3H_7)_4$ are dissolved into anhydrous ethanol to form a precursor solution with a concentration of 0.1-0.5 mole/L. Then the deionized water solution with ethanol was added into the precursor solution with stirring, the mixed solution is obtained, and then DMF is added to the mixed solution to form a composite solution. The molar ratio of components in the composite solution is: the amount of precursor solution: the amount of ethanol in deionized water solution: the amount of deionized water: the amount of DMF=1:1-4:5-10:0.2-0.4; The 1-5 wt % of micrometer or nanopore forming additives is added into the composite solution with stirring for 10-15 minutes, and finally sealed and parked at room temperature for 0.5-2 hours, the yttrium partially stabilized zirconia coating solution with micron or nano-pore additives is obtained.

5.2.2 An Example of Manufacturing Process for Yttrium Partially Stabilized Zirconia Organic Precursor Coating Solution B 2-ethylhexanoate containing metal ions Zr and Y was selected as precursor materials such as yttrium 2-ethylhexanoate $Y(C_7H_5COO)_3$ and zirconium 2-ethylhexanoate $Zr(C_7H_{15}COO)_4$. The precursor materials of yttrium 2-ethylhexanoate $Y(C_7H_{15}COO)_3$, zirconium 2-ethylhexanoate $Zr(C_7H_{15}COO)_4$ are dissolved in the solvent of 2-ethylhexanoic acid and toluene to prepare the precursor solution with the concentration of 0.1-0.5 mole/L, in which the molar ratio of 2-ethylhexanoic acid to toluene was 1:1-2; then 1-5 wt % of micrometer or nanometer pore-forming additives are added into the precursor solution with stirring at 60-80° C. for 10-30 minutes to form a uniform and transparent organic precursor solution; after that the organic precursor solution has been parked in a sealed chamber for 0.5-2 hours, the yttrium partially stabilized zirconia organic precursor solution with micron or nano-pore additives is obtained.

5.3 The Examples of Manufacturing Processes of Alumina-Doped Yttrium Partially Stabilized Zirconia Organic Precursor Coating Solution 5.3.1 An Example of Manufacturing Process of Alumina-Doped Yttrium Partially Stabilized Zirconia Organic Precursor Coating Solution a The metal alcohols salts containing metal ions Al, Zr and Y, such as $Y(OC_3H_7)_3$, $Al(OC_3H_7)_3$, $Zr(OC_3H_7)_4$ and so on are selected as precursor materials. The precursor materials of $Y(OC_3H_7)_3$, $Al(OC_3H_7)_3$, $Zr(OC_3H_7)_4$ are dissolved into anhydrous ethanol to form a precursor solution with a concentration of 0.1-0.5 mole/L; and then the precursor solution was added to a deionized water and ethanol solution with stirring to obtain a mixed solution, and then DMF is added to the mixed solution to form a composite solution. The molar ratio of the components in the composite solution is: the amount of precursor solution: the amount of ethanol in the deionized water and ethanol solution: the amount of deionized water: the amount of DMF=1:1-4:5-10:0.2-0.4; Then 1-5 wt % of micrometer or nanopore-forming additives are added into the composite solution with stirring for 10-15 minutes, and finally the precursor solution has been sealed and parked at room temperature for 0.5-2 hours, the aluminum oxide doped yttrium partially stabilized zirconia organic precursor coating solution with micron or nano-pore additives is obtained.

5.3.2 An Examples of Manufacturing Process for Alumina-Doped Yttrium Partially Stabilized Zirconia Organic Precursor Coating Solution B 2-ethylhexanoate containing metal ions Al, Zr and Y are selected as precursor materials such as yttrium 2-ethylhexanoate $Y(C_7H_{15}COO)_3$, aluminum 2-ethylhexanoate $Al(C_7H_{15}COO)_3$ and zirconium 2-ethylhexanoate $Zr(C_7H_{15}COO)_4$. The precursor materials Yttrium 2-ethylhexanoate $Y(C_7H_{15}COO)_3$, Aluminum 2-ethylhexanoate $Al(C_7H_{15}COO)_3$, Zirconium 2-ethylhexanoate $Zr(C_7H_{15}COO)_4$ are dissolved in the solvent of 2-ethylhexanoic acid and toluene to prepare the precursor solution with concentration of 0.1-0.5 mole/L, in which the molar ratio of 2-ethylhexanoic acid to toluene is 1:1-2; adding 1-5 wt % of micrometer or nanometer pore-forming additives into the precursor solution with stirring for 10-30 minutes at 60-80° C. to form a uniform and transparent organic precursor solution, then the organic precursor solution is sealed and parked at room temperature for 0.5-2 hours the alumina-doped yttrium partially stabilized zirconia organic precursor solution with micron or nano-pore additives is obtained.

6. The Examples of Manufacturing Processes for Bioengineering Materials Coated by Biomimetic Micro-Nano Pore Gradient Alumina, Yttrium Partially Stabilized Zirconia and Alumina Doped with Yttrium Partially Stabilized Zirconia Films 6.1 The Examples of Manufacturing Processes for Bio-engineering Materials and Products of Alumina, Yttrium Partially Stabilized Zirconia and Alumina Doped Yttrium Partially Stabilized Zirconia Substrates Coated by a Biomimetic Micro-Nanoporous Gradient Alumina Film.

6.1.1 An Example 1 of Manufacturing Process for an Abnormal Macrostructure of Bio-Engineering Materials and Products Such as Alumina, Yttrium-Partially Stabilized Zirconia and Alumina-Doped Yttrium-Partially Stabilized Zirconia Substrates Coated by a Biomimetic Micro-Nanoporous Gradient Alumina Film. (FIGS. 1 and 3).

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The computer aided machining (CAM) is used to form the required special-shaped surface with micro-structure of 0.3-0.5 micron. The substrates is heated at the rate of 1-10° C./s to 120-200° C. for drying of 1-2 hours and the surface humidity is controlled. The substrates has been coated by alumina organic precursor coating solution with nano-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products such as alumina, yttrium-partially stabilized zirconia and alumina-doped yttrium-partially stabilized zirconia substrates coated by a biomimetic micro-nanoporous gradient alumina film are obtained. (FIG. 1 and FIG. 3)

6.1.2 An Example 2 of Manufacturing Process for an Abnormal Macrostructure of Bio-Engineering Materials and Products Such as Alumina Yttrium-Partially Stabilized Zirconia and Alumina-Doped Yttrium-Partially Stabilized Zirconia Substrates Coated by a Biomimetic Micro-Nanoporous Gradient Alumina Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The computer aided machining (CAM) is used to form the required special-shaped surface with micro-structure of 0.3-0.5 micron. The substrates is heated at the rate of 1-10° C./s to 120-200° C. for drying of 1-2 hours and continues increase the temperature at a rate of 10-50° C./s to 700-1100° C. for pre-sintering of 1-2 hours; After cooling dawn, the substrates with coatings cleaned by water with ultrasonic wave, dry, and clean with acetone. The substrates has been coated by alumina organic precursor coating solution A with nano-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products such as alumina, yttrium-partially stabilized zirconia and alumina-doped yttrium-partially stabilized zirconia substrates coated by a biomimetic micro-nanoporous gradient alumina film are obtained.

Figure 4:
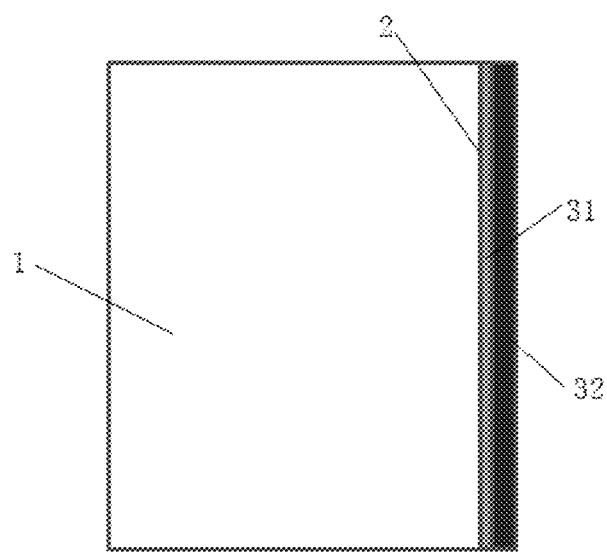
FIG. 4 is bioengineering materials and products with a smooth surface coated by a biomimetic micro-nanopore gradient film.

6.1.3 An Example 2 of Manufacturing Process for a Smooth Surface of Bio-Engineering Materials and Products Such as Alumina, Yttrium-Partially Stabilized Zirconia and Alumina-Doped Yttrium-Partially Stabilized Zirconia Substrates Coated by a Biomimetic Micro-Nanoporous Gradient Alumina Film. (FIGS. 2 and 4).

The difference between this example and 6.1.1 is that the required smooth surface is formed on the bio-engineering materials and products by computer-aided design (CAD) and computer-aided processing (CAM), the others are the same as 6.1.1.

6.1.4 An Example 2 of Manufacturing Process for a Smooth Surface of Bio-Engineering Materials and Products Such as Alumina Yttrium-Partially Stabilized Zirconia and Alumina-Doped Yttrium-Partially Stabilized Zirconia Substrates Coated by a Biomimetic Micro-Nanoporous Gradient Alumina Film.

The difference between this example and 6.1.2 is that the required smooth surface is formed on the bio-engineering materials and products by computer-aided design (CAD) and computer-aided processing (CAM), and the others are the same as 6.1.2.

Figure 5:
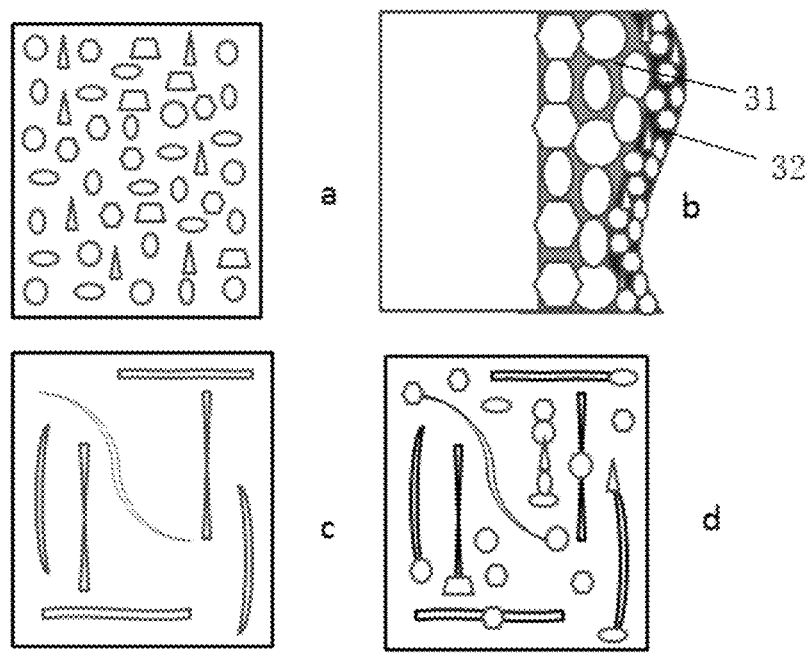
FIG. 5 is the biomimetic micron-nanopore structures of the invention.

6.1.5 An Example 5 of Manufacturing Process for a Profiled Surface of Bio-Engineering Materials and Products Such as Alumina Yttrium-Partially Stabilized Zirconia and Alumina-Doped Yttrium-Partially Stabilized Zirconia Substrates Coated by a Biomimetic Micro-Nanoporous Gradient Alumina Film. (FIG. 5).

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The computer aided machining (CAM) is used to form the required a profiled surface. The substrates is heated at the rate of 1-10° C. is to 120-200° C. for drying of 1-2 hours and the surface humidity is controlled. The substrates has been coated by alumina organic precursor coating solution A with micron-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; The substrates with coatings continues increase the temperature at a rate of 10-50° C./s to 700-1100° C. for pre-sintering of 1-2 hours; After cooling dawn, the substrates with coatings cleaned by water with ultrasonic wave, dry, and clean with acetone. The substrates has been coated by alumina organic precursor coating solution A with nano-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products with a profiled surface such as alumina, yttrium-partially stabilized zirconia and alumina-doped yttrium-partially stabilized zirconia substrates coated by a biomimetic micro-nanoporous gradient alumina film are obtained.

6.1.6 An Example 6 of Manufacturing Process for a Smooth Surface of Bio-Engineering Materials and Products Such as Alumina, Yttrium-Partially Stabilized Zirconia and Alumina-Doped Yttrium-Partially Stabilized Zirconia Substrates Coated by a Biomimetic Micro-Nanopore Gradient Alumina Film.

The difference between this example and 6.1.5 is that the required smooth surface is formed on the bio-engineering materials and products by computer-aided design (CAD) and computer-aided processing (CAM), and the others are the same as 6.1.5.

6.1.7 An Example 7 of Manufacturing Process for a Profiled Surface of Bio-Engineering Materials and Products Such as Alumina Yttrium-Partially Stabilized Zirconia and Alumina-Doped Yttrium-Partially Stabilized Zirconia Substrates Coated by a Biomimetic Micro-Nanoporous Gradient Alumina Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The substrates is heated at the rate of 1-10° C./s to 120-200° C. for drying of 1-2 hours. The computer aided machining (CAM) is used to form the required a profiled surface. The surface humidity is controlled. The substrates has been coated by alumina organic precursor coating solution A with micron-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products with a profiled surface such as alumina, yttrium-partially stabilized zirconia and alumina-doped yttrium-partially stabilized zirconia substrates coated by a biomimetic micro-nanoporous gradient alumina film are obtained.

6.2 The Examples of Manufacturing Processes for Bioengineering Materials and Products of Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

6.2.1 An Example 1 of Manufacturing Process for Bioengineering Materials and Products with a Profiled Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The computer aided machining (CAM) is used to form the required a profiled surface of the substrates. The substrates is heated at the rate of 1-10° C./s to 120-200° C. for drying of 1-2 hours, and the surface humidity is controlled. The substrates has been coated by yttrium partially stabilized zirconia organic precursor coating solution A with micron-pore additives using dipping, spraying and rotating coating methods, and the redundant solution is removed. After drying at 120-200° C. for 10 minutes, and repeating the above steps, the more coatings with thickness of 0.3-3 microns are obtained; When the yttrium partially stabilized zirconia organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products with a profiled surface such as alumina, yttrium-partially stabilized zirconia and alumina-doped yttrium-partially stabilized zirconia substrates coated by a biomimetic micro-nanoporous gradient yttrium partially stabilized zirconia film are obtained.

6.2:2 an Example 2 of Manufacturing Process for Bioengineering Materials and Products with a Special Macrostructure Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The computer aided machining (CAM) is used to form the required a special macrostructure surface with 0.3-0.5 micron of the substrates. The substrates is heated at the rate of 1-10° C./s to 120-200° C. for drying of 1-2 hours, and continues increase the temperature at a rate of 10-50° C./s to 700-1100° C. for pre-sintering of 1-2 hours; After cooling dawn, the substrates with coatings cleaned by water with ultrasonic wave, dry, and clean with acetone. The substrates has been coated by yttrium partially stabilized zirconia organic precursor coating solution A with nano-pore additives using clipping, spraying and rotating coating methods, and the redundant solution is removed. After drying at 120-200° C. for 10 minutes, and repeating the above steps, the more coatings with thickness of 0.3-3 microns are obtained; When the yttrium partially stabilized zirconia organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products such as alumina, yttrium-partially stabilized zirconia and alumina-doped yttrium-partially stabilized zirconia substrates coated by a biomimetic micro-nanoporous gradient yttrium partially stabilized zirconia film are obtained.

6.2.3 An Example 3 of Manufacturing Process for Bioengineering Materials and Products with a Smooth Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

The difference between this example and 6.2.1 is that the required smooth surface is firmed or the bioengineering materials and products by computer aided design (CAD) and computer-aided processing (CAM), and the others are the same as 6.2.1.

6.2.4 An Example 4 of Manufacturing Process for Bioengineering Materials and Products with a Smooth Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

The difference between this example and 6.2.2 is that the required smooth surface is formed on the bioengineering materials and products by counting computer-aided design (CAD) and computer-aided processing (CAM), and the others are the same as 6.2.2.

6.2.5 An Example 5 of Manufacturing Process for Bioengineering Materials and Products with a Profiled Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The substrates is heated at the rate of 1-10° C. is to 120-200° C. for drying of 1-2 hours; After cooling down, the computer aided machining (CAM) is used to form the required a profiled surface. The surface humidity of the substrates is controlled. The substrates has been coated by yttrium partially stabilized zirconia organic precursor coating solution A with micron-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with micron-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; The substrates with coatings continues increase the temperature at a rate of 10-50° C./s to 700-1100° C. for pre-sintering of 1-2 hours; After cooling dawn, the substrates with coatings cleaned by water with ultrasonic wave, dry, and clean with acetone. The substrates has been coated by yttrium partially stabilized zirconia organic precursor coating solution A with nano-pore additives using dipping, spraying and rotating coating methods, and the redundant solution is removed. After drying at 120-200° C. for 10 minutes, and repeating the above steps, the more coatings with thickness of 0.3-3 microns are obtained; When the yttrium partially stabilized zirconia organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products with a profiled surface such as alumina, yttrium-partially stabilized zirconia and alumina-doped yttrium-partially stabilized zirconia substrates coated by a biomimetic micro-nanoporous gradient yttrium partially stabilized zirconia film are obtained.

6.2.6 An Example 6 of Manufacturing Process for Bioengineering Materials and Products with a Smooth Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

The difference between this example and 6.2.5 is that the required smooth surface is formed on the bioengineering materials and products by computer-aided design (CAD) and computer-aided processing (CAM), and the others are the same as 6.2.5.

6.2.7 An Example 7 of Manufacturing Process for Bioengineering Materials and Products with a Profiled Surface Such as Alumina, Yttrium Partially Stabilized Zirconia and Alumina Doped Yttrium Partially Stabilized Zirconia Substrates Coated by a Biomimetic Micro-Nanoporous Gradient Yttrium Partially Stabilized Zirconia Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The substrates is heated at the rate of 1-10° C. is to 120-200° C. for drying of 1-2 hours; After cooling down, the computer aided machining (CAM) is used to form the required a profiled surface. The surface humidity of the substrates is controlled. The substrates has been coated by yttrium partially stabilized zirconia organic precursor coating solution A with micron-pore additives using dipping, spraying and rotating coating methods, and the redundant solution is removed. After drying at 120-200° C. for 10 minutes, and repeating the above steps, the more coatings with thickness of 0.3-3 microns are obtained; When the organic precursor solution B with micron-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained; When the organic precursor solution B with nano-pore additives is used for coating processes by immersion dipping, spraying, and rotating coating methods, the excess solution is removed. Then the wet gel film is directly placed on the heater at 220-250° C. for 3-5 minutes, and the solvent is removed rapidly. Repeating the above steps, the more coatings with thickness of 0.3-3 microns are obtained;

Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bio-engineering materials and products with a profiled surface such as alumina, yttrium-partially stabilized zirconia and alumina-doped yttrium-partially stabilized zirconia substrates coated by a biomimetic micro-nanoporous gradient yttrium partially stabilized zirconia film are obtained.

6.3 The Examples of Manufacturing Processes for Bioengineering Materials and Products of Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

6.3.1. An Example 1 of Manufacturing Process for Bioengineering Materials and Products with an Abnormal Macrostructure Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.2.1 is that the yttrium partially stabilized zirconia organic precursor solution is replaced by the alumina doped yttrium partially stabilized zirconia organic precursor solution, and the others are the same as 6.2.1.

6.3.2 An Example 2 of Manufacturing Process for Bioengineering Materials and Products with an Abnormal Macrostructure Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.2.2 is that the yttrium partially stabilized zirconia organic precursor solution is replaced by the alumina doped yttrium partially stabilized zirconia organic precursor solution, and the others are the same as 6.2.2.

6.3.3 An Example 3 of Manufacturing Process for Bioengineering Materials and Products with an Smooth Surface Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.3.1 is that the required smooth surface is formed on the bioengineering materials and products by computer-aided design (CAD) and computer-aided processing (CAM), and the others are the same as 6.3.1.

6.3.4 An Example 4 of Manufacturing Process for Bioengineering Materials and Products with an Smooth Surface Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.3.2 is that the required smooth surface is formed on the bioengineering materials and products by computer-aided design (CAD) and computer-aided processing (CAM), and the others are the same as 6.3.2.

6.3.5 An Example 5 of Manufacturing Process for Bioengineering Materials and Products with an Profiled Surface Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.2.5 is that the yttrium partially stabilized zirconia organic precursor solution is replaced by the alumina doped yttrium partially stabilized zirconia organic precursor solution, and the others are the same as 6.2.5.

6.3.6 An Example 6 of Manufacturing Process for Bioengineering Materials and Products with a Smooth Surface Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.3.5 is that the required smooth surface is formed on the bioengineering materials and products by computer aided design (CAD) and computer aided processing (CAM), and the others are the same as 6.3.5.

6.3.7 An Example 7 of Manufacturing Process for Bioengineering Materials and Products with a Profiled Surface Such as Alumina, Yttrium Partially Stabilized Zirconia and Alumina Doped Yttrium Partially Stabilized Zirconia Substrates Coated by a Biomimetic Micro-Nanoporous Gradient Alumina Doped Yttrium Partially Stabilized Zirconia Film.

The difference between this example and 6.2.7 is that the yttrium partially stabilized zirconia organic precursor solution is replaced by the alumina doped yttrium partially stabilized zirconia organic precursor solution, and the others are the same as 6.2.7.

6.4 The Examples of Manufacturing Processes for Bioengineering Materials and Products Such as Alumina, Yttrium Partially Stabilized Zirconia and Alumina Doped Yttrium Partially Stabilized Zirconia Substrates with a Profiled Surface or Micron Surface Structure or Smooth Surface Coated by Composite Thin Films from Biomimetic Micro-Nanoporous Gradient Alumina Film, Yttrium Partially Stabilized Zirconia Film, and Alumina Doped Yttrium Partially Stabilized Zirconia Film.

Aluminum oxide, yttrium partially stabilized zirconia and yttrium doped yttrium partially stabilized zirconia powders are prepared by co-precipitation method and hydrothermal decomposition method. Aluminum oxide, yttrium partially stabilized zirconia and yttrium doped yttrium partially stabilized zirconia substrates are prepared by forming methods. The substrates is heated at the rate of 1-10° C./s to 120-200° C. for drying of 1-2 hours; After cooling down, the computer aided machining (CAM) is used to form the required a profiled surface or micron surface structure or smooth surface. The surface humidity of the substrates is controlled. The substrates has been coated or alternatively coated by one of following organic precursor coating solutions such as alumina organic precursor coating solution A, yttrium partially stabilized zirconia organic precursor coating solution A, and alumina doped yttrium partially stabilized zirconia organic precursor coating solution A, which have micron-pore additives and nano-pore additives and used clipping, spraying and rotating coating methods, and the redundant solution is removed. After drying at 120-200° C. for 10 minutes, and repeating the above steps, the more coatings with thickness of 0.3-3 microns are obtained; When the substrates has been coated or alternatively coated by one of following organic precursor coating solutions such as alumina organic precursor coating solution B, yttrium partially stabilized zirconia organic precursor coating solution B, and alumina doped yttrium partially stabilized zirconia organic precursor coating solution B, which have micron-pore additives and nano-pore additives and used clipping, spraying and rotating coating methods, and the redundant solution is removed. Then the wet gel film is directly placed on the heater at 220-250° C. for 3-5 minutes, and the solvent is removed rapidly. Repeating the above steps, the more coatings with thickness of 0.3-3 microns are obtained; Before firing, the furnace is pre-fired to 50-60 C, and the firing processes of the biomedical engineering materials with coatings are divided into three steps: The first step, the biomedical engineering materials with coatings are heated at a rate of 1-5° C./min up to 250-350° C., and hold for 0.5-1 h in mild oxidizing atmosphere; The second step, the temperature rises a rate is 5-10° C./min up to 500-600° C. and hold for 1-2 hours in strong oxidizing atmosphere; The third step, the temperature is increased rapidly at a rate of 50-100° C./s up to 1400-1700° C. and hold for 1-2 hours, and then the temperature is cooled to room temperature naturally. Finally, the biomedical engineering materials with coatings are cleaned by SC1 cleaning, SC2 cleaning, SC3 cleaning and acetone, alcohol and distilled water for ultrasonic cleaning for 10-30 minutes respectively. The bioengineering materials and products such as alumina, yttrium partially stabilized zirconia and alumina doped yttrium partially stabilized zirconia substrates with a profiled surface or micron surface structure or smooth surface coated by composite thin films from biomimetic micro-nanoporous gradient alumina film, yttrium partially stabilized zirconia film, and alumina doped yttrium partially stabilized zirconia film.

In the invention, the strength and toughness of biomedical engineering materials with zirconia-based coatings are 800 Mpa-1200 Mpa and 10.0 Mpa·m$^{1/2}$-20 Mpa·m$^{1/2}$.

Animal experiments show that these nano-oxide ceramic films have very good biocompatibility and biological activity.

White the invention has been described with reference to exemplary embodiments, it will be understood by those skilled in the art that various changes may be made and equivalents maybe substituted for elements thereof without departing from the scope of the invention. In addition, many modifications may be made to adapt a particular situation or materials to the teachings of the invention without departing from the essential scope thereof. Therefore, it is intended that the invention not be limited to the particular embodiment disclosed as the best mode contemplate for carrying out this invention, but that the invention will include all embodiments falling within the scope of the appended embodiments.

What is claimed is:

1. A method of forming a biomimetic micro-nano porous oxide ceramic film, the method comprising: providing a biomedical surface structure; coating the surface structure with an inorganic precursor coating solution selected from the group consisting of nanometer alumina suspension slurry, yttrium partially stabilized zirconia suspension slurry, or alumina-doped yttrium partially stabilized zirconia suspension slurry; drying and sintering the coated surface structure; cooling the coated surface structure; and, forming a film selected from the group consisting of a single film, formed directly on the surface structure, having a nanopore outer layer or a double film, formed directly on the surface structure, having permanent micropore inner layer and a nanopore outer layer, wherein coating the surface structure with an inorganic precursor coating solution includes the substeps of: subsequent to coating, heating at a rate of 1-10 C/s to 120-200° for a drying of 1-2 hours; repeating the steps of coating and heating; pre-sintering at a rate of 10-50° C./s to 700-1100° C. for 1-2 hours; coating and heating at a rate of 1-10 C/s to 120-200° C. for a drying of 1-2 hours; repeating the steps of coating and heating; sintering at a rate of 1-10° C./s to 1400-1700° C. for 2-3 hours, creating a film selected from the group consisting of a single film with nanopores having a thickness of 0.3-3 microns or a double film having a microporous inner layer thickness of 0.3-3 microns, and a nanoporous outer layer thickness of 0.3-3 microns.

2. The method of claim 1 wherein coating the surface structure with nanometer alumina suspension slurry includes coating using a method selected from the group consisting of liquid phase coprecipitation or hydrothermal-hydrolysis.

3. The method of claim 2 wherein coating the surface structure using the liquid phase coprecipitation method includes:
providing an aluminum solution selected from the group consisting of aluminum hydroxide suspension, aluminum chloride, and aluminum nitrate solution, with an ammonium hydroxide precipitate;
dripping the precipitate into the aluminum solution to create an alumina precursor;
mixing the alumina precursor with a dispersant and water to create a slurry with 2-15 vol % of solid phase;
adjusting the pH of the slurry to 8-10;
adding 1-5 wt % of pore forming additives to obtain a nano-sized alumina suspension slurry;
wherein coating the surface structure using the hydrothermal-hydrolysis method includes:
heating a 0.5-1 mold, aluminum hydroxide suspension at 40-60° C. for 2-3 hours;
adding 0.5-1 wt % of dispersant and heating to 200-250° C., at a pressure of 2-3 MPa for 55-65 hours, to gradually hydrolyze a precipitant;
centrifuging, filtering in vacuum, washing with distilled water and ethanol, and drying to obtain an alumina precursor;
mixing the alumina precursor with a dispersant and water to create a slurry with 2-15 vol % of solid phase;
adjusting the pH of the slurry to 8-10; and,
adding 1-5 wt % of pore forming additives to obtain a nano-sized alumina suspension slurry.

4. The method of claim 1 wherein coating the surface structure with the yttrium partially stabilized zirconia suspension slurry includes coating using a method selected from the group consisting of liquid phase coprecipitation or hydrothermal-hydrolysis.

5. The method of claim 4 wherein coating the surface structure with the yttrium partially stabilized zirconia suspension slurry using the liquid phase coprecipitation method includes;
providing a zirconium solution selected from the group consisting of zirconium hydroxide suspension, zirconium chloride solution, and zirconium nitrate solution;
providing a yttrium solution selected from the group consisting of yttrium hydroxide suspension, yttrium chloride solution; and yttrium nitrate solution, with an ammonium hydroxide precipitate;
dripping the precipitate into a mixed zirconium with 2-6 mol % of yttrium content solution, creating a yttrium partially stabilized zirconia precursor;
mixing the yttrium partially stabilized zirconia precursor with a dispersant and water to create a slurry with 2-15 vol % of solid phase content;
adjusting the pH of the slurry to 8-10 and adding 1-5 wt % of pore forming additives to obtain a nano-sized yttrium partially stabilized zirconia suspension slurry;
wherein coating the surface structure with the yttrium partially stabilized zirconia suspension slurry includes using a first hydrothermal-hydrolysis method as follows:
providing a zirconium hydroxide suspension with a concentration of 0.5-1 mon;
adding yttrium oxide and heating at 40-60° C. for 2-3 hours;
adding 0.5-1 wt % of dispersant and heating at 200-250° C. with a pressure of 2-3 MPa for 55-65 hours, to hydrolyze a precipitate;
centrifuging, filtering in vacuum, washing with distilled water and ethanol, and drying the precipitate to obtain a yttrium-stabilized zirconia precursor with yttrium content of 2-6 mol %;
mixing the yttrium-stabilized zirconia precursor with a dispersant and water to form a slurry with a 2-15 vol % of solid content;
adjusting the slurry pH to 8-10 and adding 1-5 wt % of pore forming additives to obtain a nano-sized yttrium-stabilized zirconia slurry with a yttrium content of 2-6 mol %;
wherein coating the surface structure with the yttrium partially stabilized zirconia suspension slurry includes using a second hydrothermal-hydrolysis method as follows:
mixing a 0.5-0.6 mold, zirconium oxychloride solution and 1 mol/L carbonyl two amine with volume ratio of 1:1, to form a reaction liquid;
heating the reaction liquid to form a zirconium hydroxide gel;
mixing the gel with the reaction liquid with a weight ratio of 1:1;
under stirring conditions, forming a hydrous zirconia sol by hydrolysis at a boiling temperature of 100-150 C;
adding 2-6 mol % of yttrium nitrate solution to the hydrated zirconia sol;
dissolving the yttrium nitrate and hydrolyzed to form a precipitate;
centrifuging, filtering in vacuum, washing with distilled water and ethanol, and drying the precipitate to obtain a yttrium-stabilized zirconia precursor with yttrium content of 2-6 mol %;
mixing the yttrium-stabilized zirconia precursor with a dispersant and water to form a slurry with 2-15 vol % of solid content; and,
adjusted the slurry pH to 8-10 and adding 1-5 wt % of pore forming additives, to create a nano-sized yttrium-stabilized zirconia slurry with a yttrium content of 2-6 mol %.

6. The method of claim 1 wherein coating the surface structure with the alumina-doped yttrium partially stabilized zirconia suspension slurry includes coating using a method selected from the group consisting of liquid phase coprecipitation or hydrothermal-hydrolysis.

7. The method of claim 6 wherein coating the surface structure with the alumina-doped yttrium partially stabilized zirconia suspension slurry using the liquid phase coprecipitation method includes:
providing a zirconium solution selected from the group consisting of zirconium hydroxide suspension, zirconium chloride solution, and zirconium nitrate solution;
providing a yttrium solution selected from the group consisting of yttrium hydroxide suspension, yttrium chloride solution, and yttrium nitrate solution;
providing an aluminum solution selected from the group consisting of aluminum hydroxide suspension, aluminum chloride suspension, and aluminum nitrate suspension, with an ammonium hydroxide precipitate;
dripping the precipitate into a mixture of 1-5 mol % aluminum and zirconium with 2-6 mol % of yttrium content solution, creating an alumina-doped yttrium partially stabilized zirconia precursor;

mixing the alumina-doped yttrium partially stabilized zirconia precursor with a dispersant and water to create a slurry with 2-15 vol % of solid phase content;

adjusting the pH of the slurry to 8-10 and adding 1-5 wt % of pore forming additives to obtain a nano-sized alumina-doped yttrium partially stabilized zirconia suspension slurry;

wherein coating the surface structure with the alumina-doped yttrium partially stabilized zirconia suspension slurry includes using a first hydrothermal-hydrolysis method as follows:

providing an aluminum mixed zirconium hydroxide suspension with concentration of 0.5-1 mol/L;

adding yttrium oxide and heating at 40-60° C. for 2-3 hours;

adding 0.5-1 wt % of dispersant and heating at 200-250° C. with a pressure of 2-3 MPa for 55-65 hours, to hydrolyze a precipitate;

centrifuging, filtering in vacuum, washing with distilled water and ethanol, and drying the precipitate to obtain an alumina-doped yttrium-stabilized zirconia precursor with 1-5 mol % aluminum and a yttrium content of 2-6 mol %;

mixing the alumina-doped yttrium-stabilized zirconia precursor with a dispersant and water to form a slurry with a 2-15 vol % of solid content;

adjusting the slurry pH to 8-10 and adding 1-5 wt % of pore forming additives to obtain a nano-sized alumina-doped yttrium-stabilized zirconia slurry with a 1-5 mol % aluminum content and a yttrium content of 2-6 mol %;

wherein coating the surface structure with the alumina-doped yttrium partially stabilized zirconia suspension slurry includes using a second hydrothermal-hydrolysis method as follows:

mixing a 1-5 mol % aluminum hydroxide and 0.5-0.6 mol/L zirconium oxychloride solution with 1 mol/L carbonyl two amine at a volume ratio of 1:1, to form a reaction liquid;

heating the reaction liquid to form an aluminum and zirconium hydroxide gel;

mixing the gel with the reaction liquid with a weight ratio of 1:1;

under stirring conditions, forming a hydrous zirconia sol by hydrolysis at a boiling temperature of 100-150 C;

adding 2-6 mol % of yttrium nitrate solution to the hydrated zirconia sol;

dissolving the yttrium nitrate and hydrolyzing to form a precipitate;

centrifuging, filtering in vacuum, washing with distilled water and ethanol, and drying the precipitate to obtain an alumina-doped yttrium-stabilized zirconia precursor with yttrium content of 2-6 mol %;

mixing the alumina-doped yttrium-stabilized zirconia precursor with a dispersant and water to form a slurry with a 2-15 vol % of solid content; and, adjusted the slurry pH to 8-10 and adding 1-5 wt % of pore forming additives, to create a nano-sized alumina-doped yttrium-stabilized zirconia slurry with an aluminum content of 1-5 mol % and a yttrium content of 2-6 mol %.

8. The method of claim 1 wherein coating the surface structure with an inorganic precursor coating solution includes coating with precursor coating solution selected from the group consisting of yttrium partially stabilized zirconia suspension slurry and alumina doped yttrium partially stabilized zirconia suspension slurry;

wherein, the yttrium is sourced from a compound selected from the group consisting of yttrium nitrate and yttrium chloride;

wherein the zirconium is sourced from a compound selected from the group consisting of zirconium hydroxide, zirconium chloride, and zirconium nitrate; and, wherein the aluminum is sourced from a compound selected from the group consisting of aluminum hydroxide, aluminum chloride, and aluminum nitrate.

9. The method of claim 1 wherein coating the surface structure with an inorganic precursor coating solution includes the selected precursor coating solution comprising:

a precipitate solution formed with an ammonium bicarbonate and ammonium hydroxide, where the concentration of ammonium bicarbonate is 10-50%; and, an additive selected from the group consisting of a micropore additive, a nanopore additive, and combinations thereof;

wherein the micropore additive is selected from the group consisting of polyethylene glycol, nitrocellulose, polyacrylic acid, polypropylene amine, polyethylene, polypropylene, polyvinyl chloride, polybutadiene, polystyrene, polyacrylonitrile, polyphenol, polyformaldehyde, polyamide, polycaprolactam, polyaromatic ether, polyaromatic amide, polyimide carbonate and methyl terephthalate, methyl acrylate, and combinations thereof; and, wherein the nanopore additive is selected from the group consisting of carbonyl diamide, ethylene, propylene, vinyl chloride, butadiene, styrene, acrylonitrile, phenol, formaldehyde, amide, caprolactam, aromatic ether, aromatic amide, imide carbonate, ethylene glycol, and combinations thereof.

10. The method of claim 1 wherein providing the biomedical surface structure includes providing a biomedical surface structure selected from the group consisting of alumina, zirconia, yttrium partially stabilized zirconia, and alumina-doped yttrium partially stabilized zirconia.

11. The method of claim 1 wherein coating the surface structure with an inorganic precursor coating solution includes the content of yttrium in the yttrium partially stabilized zirconia slurry being 2-6 mol %, and the content of aluminum in alumina-doped yttrium partially stabilized zirconia slurry being 1-5 mol % with a yttrium content of 2-6 mol %.

12. A method of forming a biomimetic micro-nano porous oxide ceramic film, the method comprising: providing a biomedical surface structure; coating the surface structure with an inorganic precursor coating solution selected from the group consisting of nanometer alumina suspension slurry, yttrium partially stabilized zirconia suspension slurry, or alumina-doped yttrium partially stabilized zirconia suspension slurry; drying and sintering the coated surface structure; cooling the coated surface structure; and, forming a film selected from the group consisting of a single film, formed directly on the surface structure, having a nanopore outer layer or a double film, formed directly on the surface structure, having permanent micropore inner layer and a nanopore outer layer, wherein coating the surface structure with an inorganic precursor coating solution includes the substeps of: subsequent to coating, heating at a rate of 1-10 C/s to 120-200° for a drying of 1-2 hours; repeating the steps of coating and heating; sintering at a rate of 1-10° C./s to 1400-1700° C. for 2-3 hours, creating a film selected from the group consisting of a single film with nanopores having a thickness of 0.3-3 microns or a double film having a microporous inner layer thickness of 0.3-3 microns, and a nanoporous outer layer thickness of 0.3-3 microns.

13. A method of forming a biomimetic micro-nano porous oxide ceramic film, the method comprising: providing a biomedical surface structure; coating the surface structure with an inorganic precursor coating solution selected from the group consisting of nanometer alumina suspension slurry, yttrium partially stabilized zirconia suspension slurry, or alumina-doped yttrium partially stabilized zirconia suspension slurry; drying and sintering the coated surface structure; cooling the coated surface structure; and, forming a film selected from the group consisting of a single film, formed directly on the surface structure, having a nanopore outer layer or a double film, formed directly on the surface structure, having permanent micropore inner layer and a nanopore outer layer, wherein drying and sintering the coated surface structure includes: ultrasonic cleaning for 10-30 minutes using a process selected from the group consisting of SC1 cleaning, SC2 cleaning, or SC3 cleaning, with acetone, alcohol, and water; wherein the SC1 cleaning solution is: $NH_4OH:H_2O_2:H_2O$ with volume ratio is 1:1-2:5-7, and the cleaning temperature is 65-80° C.; wherein the SC2 cleaning solution is: $HCl:H_2O_2:H_2O$ with volume ratio of 1:1-2:6-8, and cleaning temperature is at 65-80° C.; and, wherein the SC3 cleaning solution is: $H_2SO_4:H_2O_2:H_2O$ volume ratio is 1:1:3, and the cleaning temperature is at 100-130° C.

\* \* \* \* \*